United States Patent
Siddiqui et al.

(10) Patent No.: US 6,492,445 B2
(45) Date of Patent: Dec. 10, 2002

(54) ANTIMICROBIAL POLYMER LATEXES DERIVED FROM UNSATURATED QUATERNARY AMMONIUM COMPOUNDS AND ANTIMICROBIAL COATINGS, SEALANTS, ADHESIVES AND ELASTOMERS PRODUCED FROM SUCH LATEXES

(75) Inventors: Adnan Siddiqui, Vernon Hills, IL (US); Alfred K. Schultz, Lake Villa, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 09/874,613

(22) Filed: Jun. 5, 2001

(65) Prior Publication Data

US 2002/0040092 A1 Apr. 4, 2002

Related U.S. Application Data

(63) Continuation of application No. 09/124,418, filed as application No. PCT/US98/01492 on Jan. 28, 1998, now Pat. No. 6,242,526.
(60) Provisional application No. 60/036,505, filed on Jan. 28, 1997.

(51) Int. Cl.$^7$ ............................................... C08F 226/00
(52) U.S. Cl. ..................... 524/156; 524/547; 524/555; 524/608; 524/609; 524/748
(58) Field of Search ................................. 524/555, 156, 524/547, 608, 609, 748

(56) References Cited

U.S. PATENT DOCUMENTS 3,925,442 A * 12/1975 Samour ..................... 526/225
5,302,192 A * 4/1994 McLearie et al. ......... 106/15.05
6,017,561 A * 1/2000 Zhou et al. ................. 424/486

FOREIGN PATENT DOCUMENTS

EP          221498 A2 * 5/1987  ......... C08F/246/00

* cited by examiner

Primary Examiner—David W. Wu
Assistant Examiner—Kelechi C. Egwim
(74) Attorney, Agent, or Firm—McDonnell Boehnen Hulbert & Berghoff

(57) ABSTRACT

Antibacterial CASE materials comprising a latex comprising polymer particles and a surfactant component. Also disclosed are components and methods for forming such materials.

23 Claims, 2 Drawing Sheets

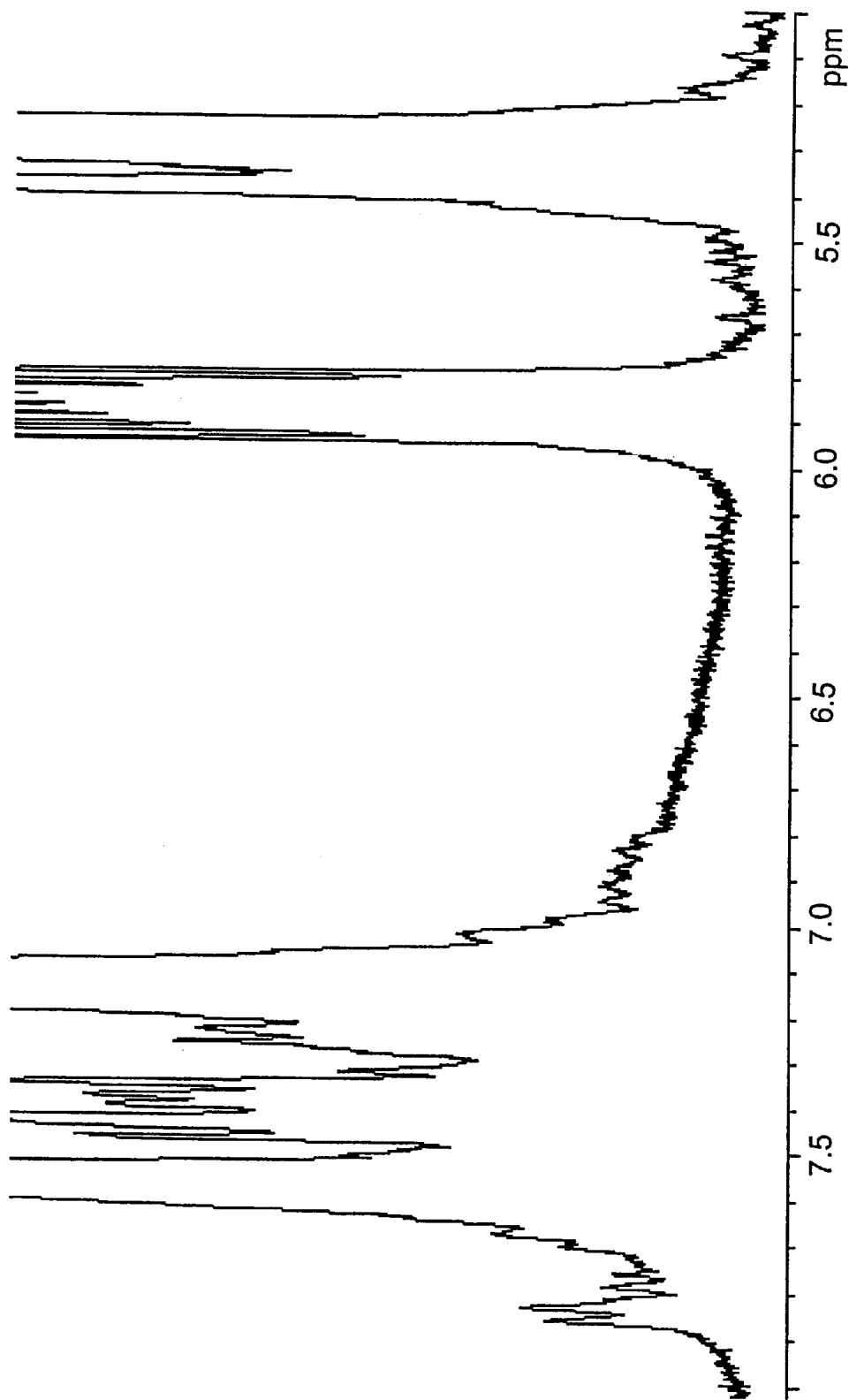
Figure I

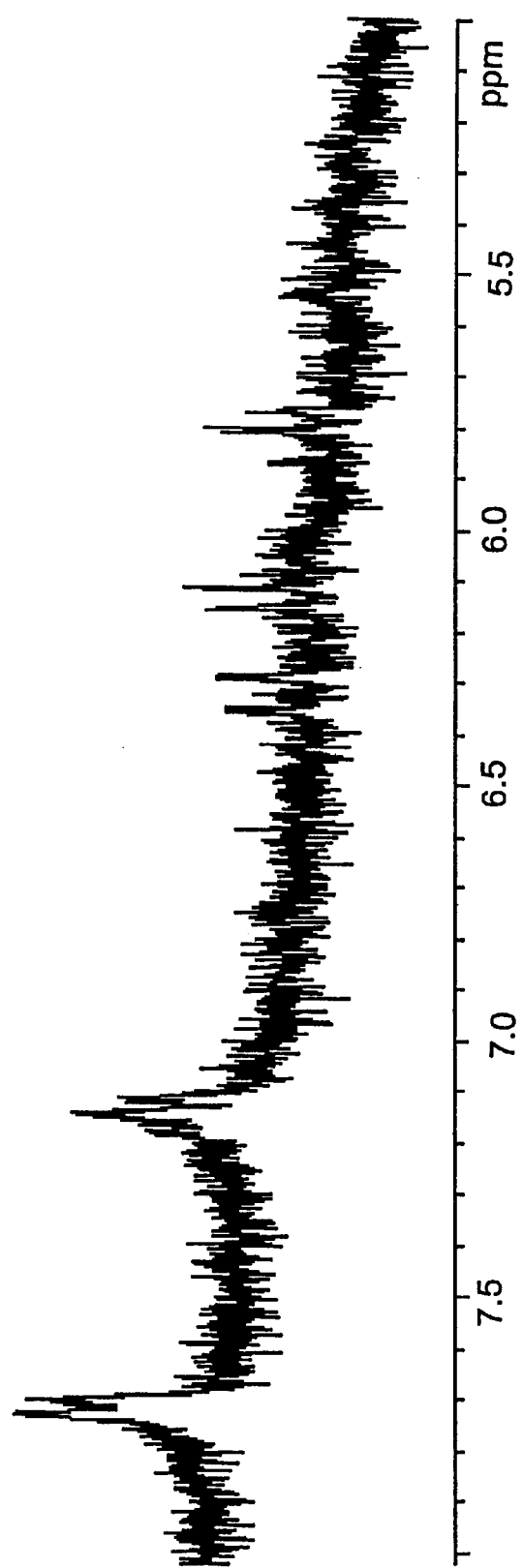
Figure II

ANTIMICROBIAL POLYMER LATEXES DERIVED FROM UNSATURATED QUATERNARY AMMONIUM COMPOUNDS AND ANTIMICROBIAL COATINGS, SEALANTS, ADHESIVES AND ELASTOMERS PRODUCED FROM SUCH LATEXES

This is a continuation of application Ser. No. 09/124,418 filed Jul. 28, 1998, U.S. Pat. No. 6,242,526, which is a 371 of International patent application Ser. No. PCT/US98/01492, filed Jan. 28, 1998, which claims benefit of U.S. provisional application Ser. No. 60/036,505, filed Jan. 28, 1997.

BACKGROUND OF THE INVENTION

1. Field of the Invention

The present invention relates to antimicrobial polymer latexes and the antimicrobial coating, adhesive, sealant and elastomer (CASE) materials derived therefrom, wherein the polymer latex is derived from various monomers and antimicrobial quaternary ammonium ethylenically unsaturated compounds. These antimicrobial quaternary ammonium ethylenically unsaturated compounds are generally derived from ethylenically unsaturated sulfonic, phosphoric and/or carboxylic acids or salts thereof, and substantially saturated antimicrobial quaternary ammonium compounds. More specifically, the invention relates to improved antimicrobial polymer latexes and CASE materials, which possess prolonged antimicrobial activity, wherein the polymers and resulting CASE materials are produced using emulsion polymerization processes which utilize antimicrobial quaternary ammonium ethylenically unsaturated compounds derived from substantially saturated antimicrobial quaternary ammonium compounds and ethylenically unsaturated alkylsulfonic acids, alkylbenzene sulfonic acids, alkyl olefin sulfonic acids, alkyl alcohol sulfuric acid esters, or alkoxylated alkyl alcohol sulfuric acid esters, fatty acids, and fatty phosphate acid esters, or salts thereof, or mixtures thereof

2. Description of the Related Art

The emulsion polymerization of ethylenically unsaturated monomers to form discrete solid polymeric particles for use in coating, adhesive, sealant, and/or elastomer (CASE) applications is well known to the art. Surfactants are commonly used materials in the manufacture of polymer latexes and various CASE products, such as, for example paints, printing inks, adhesives and pressure-sensitive adhesives. These surfactants are often indispensable for the manufacture and/or stabilization of these products in terms of processability. However, after such CASE products are used for coating, printing, adhesion or pressure bonding, the surfactants are no longer necessary, nor desirable. Rather, if the surfactant remains in the CASE product, the surfactant tends to adversely affect the resistance of the CASE material to water and even oil in many instances.

Surfactants for use in emulsion polymerization to form latexes, which are then used to prepare CASE materials, include traditional anionic surfactants, such as sodium dodecylbenzenesulfonate and nonionic surfactants such as polyoxyethylene nonylphenyl ether. However, CASE materials using polymer latex emulsions prepared using such traditional surfactants have the drawbacks of poor resistance to water and poor bond strength, typically because the surfactant remains in free form in the polymer latex and/or final CASE material. Additionally, these CASE materials often possess little or no antimicrobial activity, absent the addition of a separate antimicrobial material. When CASE materials are formulated to include such an antimicrobial material, the antimicrobial activity of the CASE material decreases reltively quickly with the passage of time and upon repeated exposure of the CASE material to various elements, including for example, water, washings with cleaning products, UV light, and the like.

CASE materials typically comprise, for example, paints (high-gloss, semi-gloss, and flat), caulks, and the like. CASE materials are typically applied to a variety of substrates, including for example, wood, metal, plastic, glass, ceramics, fiberglass, composite materials, cardboard, corrugated board, paper, textiles, non-woven materials, plastic, foam, tape or a combination thereof. Substrates can be virgin materials, i.e. materials which have not previously be treated or coated with a case material, or materials which have been previously coated or treated with a CASE material. CASE materials can be applied on top of or applied to a previously applied CASE material.

Conventional emulsion polymerization of ethylenically unsaturated monomers employs one or more surface active materials to emulsify the monomers and to stabilize the resulting polymer products, i.e., the latex. The monomers used in emulsion polymerization reactions are generally water-insoluble, but in some cases may be water-soluble. During a typical emulsion polymerization, a surfactant is used to suspend small portions of monomer in a continuous or a semi-continuous aqueous phase. Typically, the monomer molecules are dispersed or suspended as small spheres in the aqueous phase, wherein the polymerization takes place within the small spheres. The surface active agents, i.e., surfactants, typically utilized in emulsion polymerization reactions are anionic, nonionic, and cationic surfactants or a mixture thereof.

The polymeric particles formed by the emulsion polymerization process are typically utilized to prepare coating, adhesive, sealant, and/or elastomer (CASE) materials. In a traditional emulsion polymerization reaction, the surfactant does not become chemically bonded to the polymeric particles by carbon-carbon bond formation, but rather remains absorbed on the polymeric particle product solution after the emulsion polymerization reaction is complete, i.e., once all of the monomer(s) is reacted. The unreacted surfactant can have a detrimental effect on the polymer product solution, as it can interfere with the performance of such polymerization products in CASE materials; the suspension of polymeric particles may become destabilized over time and undergo unwanted coagulation. In addition, the unreacted surfactant does not provide any desireable antimicrobial activity to the CASE material. The unreacted surfactant may cause unwanted peeling of a latex paint coating on a substrate, and decreased moisture and scrubability resistance in other various CASE applications. Residual surfactant can cause an undesirable "blooming" that leads to surface irregularities in a resulting CASE material that is applied to a substrate. Additionally, residual surfactant may lead to undesirable decreases in adhesion of a particular CASE material. The traditional surfactants act as stabilizers before, during, and after polymerization, but they typically have a detrimental effect on the properties of a dry latex film, for example, due to their tendency to migrate, i.e., to leave their original positions at the latex particle surfaces and form areas of higher concentration both in pockets within the film and at the film/air and film/substrate interfaces.

Several proposals have been made in the prior art to employ a polymerizable surfactant as the surface active agent during an emulsion polymerization reaction. U.S. Pat. No. 5,478,883 (incorporated herein by reference in its entirety) describes the use of ethylenically unsaturated polymerizable water-soluble nonionic surfactants formed by the reaction of a diallylamine compound with ethylene oxide, propylene oxide or butylene oxide, in emulsion polymerization reactions. Similarly, U.S. Pat. No. 5,162,475 (incorporated herein by reference) provides alpha-beta ethylenically unsaturated poly(alkylenoxy) polymerizable surface active compounds for use in emulsion polymerization. For additional examples of polymerizable surfactants for use in emulsion polymerization processes, see U.S. Pat. Nos. 4,377,185 and 4,049,608. Also see WO8912618, EP 747456 A2, and EP 770655 A2; all describing various ethylenically unsaturated surfactant approaches to producing CASE materials with reactive surfactants. However, none of these approaches have provided an alterative to improving the CASE material and at the same time, made the polymer latex and/or the resulting case material antimicrobial, i.e. resistant to bacteria, fungi, algae, viruses, and the like.

Non-polymerizable surfactant solutions to the traditional problems encountered in performing an emulsion polymerization process are numerous. U.S. Pat. No. 3,941,857 describes the use of epoxy resins which react with the residual anionic, cationic or nonionic surfactant. Polymerizable compounds such as allyl alcohol (and esters thereof) have been found to be ineffective due to the formation of undesirable high levels of coagulum in the final emulsion polymerization product. Additionally, see U.S. Pat. Nos. 4,224,455; 5,399,617; 4,075,411; 5,344,867; 5,296,627; 5,679,732, 5,536,811; 4,912,157; and 5,039,339; and WO 97/45495.

Quaternary ammonium salt formulations have been used as disinfectants for many years and these formulations have broad spectrum antimicrobial activity. These formulations are effecatious, at higher concentrations of quaternary ammonium salts, against certain gram positive and gram negative bacteria. These formulations have also been shown to show tuberculocidal activity. These formulations have been incorporated into latex formulations to prepare a blend of latex polymer particles and quaternary ammonium compounds, wherein the resulting formulation is applied to a substrate as a CASE material. These CASE materials and the substrates treated with the CASE materials often posses excellent initial antimicrobial activity. However, upon the passage of time, exposure to the elements, exposure to water, or repeated washings, the antimicrobial activity of the CASE and/or substrate decreases. This is generally due to a washing away or removal/leaching of the quaternary ammonium compounds present in the CASE material since these quaternary agents migrate to the surface.

It is known that on the surfaces of most substrates, micro-organisms develop grow, reproduce and or thrive. These micro organisms consist of a of organic materials, bacteria, algae, protozoa or other microorganisms, depending on the substrate and the type of exposure to the enviroment of the substrate. Numerous compounds termed biocides have been proposed and used for the treatment of such substrates to kill the micro organisms. Those most commonly employed in practice are halogens or halogenated inorganic or organic derivatives, such as chlorine, bromine, iodine, potassium chloride, hypochlorous acid and its sodium or calcium salts, hypobromous acid, the salts of dichloro- and trichloroisocyanuric acids, or halogenated hydantoins; however, these compounds have the disadvantage of being corrosive and of forming chlorinated compounds which are highly toxic. It has also been proposed to use peroxygenated derivatives, phenols and phenol derivatives, heavy metals or organic derivatives thereof, formaldehyde, benzoic acid and benzoates for treatments by contact with a substrate. However, many of these compounds are expensive, and/or they leave toxic or corrosive residues on the substrate. Generally, in order to be suitable for use in an appropriate fashion in a process for the treatment of microorganisms on a substrate, a biocidal compound must have the properties of: preventing the formation of the biological micro organisms, low toxicity to humans and animals that may come in contact with the biocidal compound and/or the substrate treated with such compounds, high fungicidal, algicidal and bactericidal activity.

Thus, there is a need for emulsion polymerization latexes and processes to prepare latexes comprising polymers and discrete polymeric particles that are well suited for use in antimicrobial CASE applications. There is a specific need for antimicrobial polymer latexes and CASE materials which comprise the polymer latex, wherein the final CASE material possess low water sensitivity, improved scrubability and/or improved adhesion properties. Additionally, improved antimicrobial CASE materials with prolonged antimicrobial activity, low animal toxicity, increased latex shear stability and lowered film yellowing tendencies are highly desirable. As will be more fully described hereinafter, it has been surprisingly discovered that incorporating antimicrobial quaternary ammonium compounds into the polymer latex particles by carbon—carbon bond formation provides an antimicrobial latex polymer which can subsequently be used to prepare antimicrobial CASE materials with prolonged antimicrobial activity, The antimicrobial activity remains even after the CASE materials and the substrates treated with the CASE materials are repeatedly exposured to the elements, exposured to water, or repeatedly washing many times; i.e., the antimicrobial activity of the CASE and/or substrate remains high for an extended period of time and there is generally no washing away or significant removal/leaching of the quaternary ammonium compounds present in the CASE material.

SUMMARY OF THE INVENTION

The present invention relates to antimicrobial polymer latexes and polymer solutions and CASE materials prepared from such materials, wherein the latexes and solutions are formed using a variety of monomers in combination with a group of compounds in the form of quaternary ammonium ethylenically unsaturated compounds derived from ethylenically unsaturated sulfonic, phosphoric and/or carboxylic acids or salts thereof, or mixtures thereof, and substantially saturated quaternary ammonium compounds, wherein the quaternary ammonium ethylenically unsaturated compounds display both surface activity, i.e. they are surfactants, and antimicrobial activity. The polymer latexes, and resulting antimicrobial CASE material produced therefrom, generally possess antibacterial activity (e.g., gram negative and gram positive bacteria). These materials may also act as fungicides, mildewcides, tuberculocides, mycobacterialcides, viralcides, and the like. It has been discovered that improved antimicrobial CASE can be prepared using such antimicrobial latexes based on these antimicrobial quaternary ammonium ethylenically unsaturated compounds which function as reactive surfactants, i.e. surface active agents in polymerization processes, particularly emulsion polymerization processes. The antimicrobial CASE materials of the instant invention are based on antimicrobial quaternary ammonium ethylenically unsaturated compounds (surface active agents) which are generally capable of co-polymerizing with other ethylenically unsaturated monomers of the type which are commonly employed in polymerization processes. The polymerizable surface active agents utilized in the present invention are prepared from readily available, economical raw materials, and generally, their preparation does not require any special handling or equipment. These polymerizable surface active agents are particularly well suited for use in the formation of polymer particles which in turn may be used to prepare a variety of antimicrobial CASE materials. Surprisingly, these materials impart prolonged antimicrobial activity to the CASE materials and may also improve many of the properties of various antimicrobial CASE materials, such as for example, improved water sensitivity (i.e. they become more hydrophobic), improved scrubability, improved adhesion, increased latex shear stability, lowered film yellowing tendencies, decreased paper discoloration, and improved wet strength in paper coatings.

Examples of antimicrobial CASE materials of the instant invention include, among others, interior and exterior coatings, e.g., latex paints, container, paper and paperboard coating, e.g., can coatings, adhesives, such as water-born adhesives and pressure sensitive adhesives, sealants, industrial coatings, waxes, automotive coatings, textile coatings and binders, floor finishes, water-based inks, films, and binders and coatings for non-woven materials such as carpet backing.

The polymerizable surface active agents utilized in the instant invention may be prepared in a batch mode or a continuous mode. They may be prepared by contacting the ethylenically unsaturated acid, or a salt thereof, with a substantially saturated quaternary ammonium compound, or vise versa. The result of such contacting typically produces acid and/or salt formation, whereby such acid and/or salt may be removed by a variety of techniques know to those skilled in the art, including for example, extraction, filtration, distillation, or a combination thereof. By contacting it is meant that the ethylenically unsaturated acid(s) or salt(s) is added to the substantially saturated quaternary ammonium compound, or vise versa, and the components are mixed to effectuate the formation of an ethylenically unsaturated quaternary ammonium compound and and acid(s) or salt(s). Typically, upon mixing, the proton, or cation of the acid salt (i.e. ammonium, sodium, magnesium, potassium, calcium, and alkanolamines) and the anion of the substantially saturated quaternary ammonium compound (i.e. chloride, bromide, iodide, sulfate) exchange, with their respective counter ions to form acids and/or salts and the resulting antimicrobial ethylenically unsaturated quaternary ammonium compound.

In a less preferred embodiment, the ethylenically unsaturated quaternary ammonium compounds of the instant invention my also be derived from primary, secondary and tertiary amines and known ethylenically unsaturated quaternizing agents, such as for example, vinyl chloride. Generally, such quaternizing agents include those agents which possess ethylenically unsaturated halides, ethylenically unsaturated alkyl sulfates, and the like, which are capable of effectuating a quaternaization of an amine to produce an ethylenically unsaturated quaternary ammonium compound with antimicrobial activity.

Accordingly, an improved method is provided for forming antimicrobial CASE materials and/or polymers, utilizing antimicrobial polymerizable surface active agents detailed herein. Generally, the improved method for preparing an antimicrobial CASE material comprising:

a) preparing a mixture comprising:
  i) at least one ethylenically unsaturated monomer;
  ii) at least one antimicrobial polymerizable surface active agent;
wherein the antimicrobial polymerizable, surface active agent is a ethylenically unsaturated quaternary ammonium compound derived from:
  a) at least one acid, wherein the acid is a sulfonic acid, a carboxylic acid, or a phosphoric acid, or a salt thereof, or a mixture thereof, wherein the acid or the salt thereof contains at least one ethylenically unsaturated moiety; and
  b) at least one substantially saturated antimicrobial quaternary ammonium compound;
b) polymerizing the mixture to form a latex or mixture of polymer particles;
wherein the antimicrobial polymerizable, surface active agent is capable of polymerization with the ethylenically unsaturated monomer or co-polymerization with a partially polymerized polymer particle. Somewhat preferably, the heteroatom of the acid is linked covalently, directly or indirectly, to the ethylenically unsaturated moiety of the acid. The method may further comprise the addition of optional ingredients as detailed herein, to produce a final antimicrobial CASE product.

The polymers prepared utilizing the polymerizable surface active agents of the present invention may be used as the primary resin component or a minor resin component of a resin mixture which is used to prepare antimicrobial latexes, coatings, adhesives, sealants, elastomers, binders, inks, floor finishes and the like. A polymer is defined herein as a product produced by polymerizing two or more monomers, which may be the same or different. Additionally, the polymer may have incorporated into it, surface active agent monomers and/or homopolymeric surface active agents. The various final antimicrobial CASE materials, compositions, applications and polymer products described herein may contain various optional ingredients such as fillers, pigments, colloids, colorants, solvents, plasticizers, antioxidants, curing agents, thickeners, non-polymerizable surface active agents (surfactants), preservatives, wet strength additives, and the like.

The present invention provides an improved polymerization process for forming polymers, wherein the polymerizable surface active agent used in the polymerization reaction does not interfere with the quality of the antimicrobial CASE materials. In many cases, the quality of the antimicrobial CASE materials is improved by the use of the antimicrobial polymerizable surface active agent.

The present invention provides an improved polymerization process, wherein antimicrobial CASE materials that are formed, using the polymers of the present invention, remain uniform and stable upon the passage of time and/or exposure to moisture at ambient or elevated temperature, once the CASE material is applied to a substrate. Additionally, the antimicrobial CASE materials possess extended antimicrobial activity, over long period of time and exposure to various deleterious elements, such as for example, water, solvents, washings with cleaning products, UV light, and the like.

The present invention provides antimicrobial polymers suitable for use in antimicrobial coating, adhesive, sealant and/or elastomer (CASE) materials. The polymers may be in a variety of forms, such as, for example, solids, flakes, powders, semi-solids, thick pastes, flowable/pumpable pastes (i.e. G-phase pastes), liquids, gels, "ringing" gels, dilute or concentrated solutions and the like. The polymers may be spray dried, flaked, extruded, or the like.

The present invention additionally provides antimicrobial homopolymeric surface active agents comprised of polymerized, polymerizable surface active agents or blends of polymerizable surface active agents. These antimicrobial homopolymeric surface active agents are useful in the polymerization processes and antimicrobial CASE materials detailed herein. The present invention further provides antimicrobial homopolymeric surface active agent/polymerizable surface active agent blends comprised of partially polymerized, polymerizable surface active agents and non-polymerized, polymerizable surface active agents. These antimicrobial homopolymeric/polymerizable surface active agent blends are also useful in the polymerization processes and antimicrobial CASE materials detailed herein.

The improved polymerization process for forming antimicrobial CASE materials of the present invention preferably does not require the use of a surfactant which contains residual formaldehyde or other low molecular weight volatile organic compounds. However, while not desirable, low molecular weight volatile organic compounds, solvents and/or residual formaldehyde may be present in the polymerization products of the present invention. Further, the polymerization process of the present invention provides latexes useful in antimicrobial CASE materials with extended antimicrobial activity. Additional benefits of improved shear stability, improved pH stability, improved shelf storage stability and improved ease of viscosity modification may also be provided.

The antimicrobial polymerizable surface active agent may be added to the emulsion polymerization mixture in a batch mode (i.e. all at once), a continuous mode (i.e. by addition of an amount of the polymerizable surface active agent throughout the polymerization) or in a semi-continuous mode (i.e. addition of portions of the polymerizable surface active agent at various times during the polymerization). In a less preferred embodiment, the antimicrobial polymerizable surface active agent may be prepared in situ in the emulsion polymerization mixture, by adding at least one acid, wherein the acid is a sulfonic acid, a carboxylic acid, or a phosphoric acid, or a salt thereof, or a mixture thereof, wherein the acid or the salt thereof contains at least one ethylenically unsaturated moiety, to the mixture, followed by concurrent or step-wise addition of at least one substantially saturated antimicrobial quaternary ammonium compound, wherein the polymerizable surface active agent is formed in the mixture, with subsequent acid/salt formation.

The antimicrobial polymerizable surface active agents utilized in the present invention are generally formed by combining at least one acid, wherein the acid is a sulfonic acid, a carboxylic acid, or a phosphoric acid, or a salt thereof, or a mixture thereof, wherein the acid or the salt thereof contains at least one ethylenically unsaturated moiety; and at least one substantially saturated antimicrobial quaternary ammonium compound. The antimcrobial polymerizable surface active agents of the present invention are preferably in the form of quaternary ammonium compounds. The surface active agents of the present invention are prepared from readily available, economical raw materials, and generally, their preparation does not require any special handling or equipment.

The antimicrobial polymerizable surface active agents and blends of these surface active agents may be prepared in a variety of forms, including but not limited to, liquids, solutions, solids, powders, flakes, semi-solids, gels, "ringing" gels, G-phase liquids, hexagonal phase solids, or thick pastes. The antimicrobial polymerizable surface active agents may be spray dried, flaked, extruded, and the like. Although not critical to the present invention, the antimicrobial polymerizable surface active agents may be prepared "neat" or in a conventional solvent such as water, low molecular weight alcohol or hydrocarbon, or a mixture thereof, to produce a solution of the surface active agent. The present invention encompasses antimicrobial surface active agents as quaternary ammonium compounds in dry form and as aqueous solutions. The antimicrobial quaternary ammonium compounds may be isolated by drying a solution of the surface active agents; a solution of surface active agents may be prepared by dissolving the quaternary ammonium compound in water, low molecular weight alcohol or hydrocarbon, or a mixture thereof.

Individual antimicrobial polymerizable surface active agents of the present invention may be prepared and mixed together to produce a surface active mixture comprising "neat" surface active agents or an aqueous surfactant blend. Additionally, neat or aqueous blends of the antimicrobial polymerizable surface active agents may be prepared by contacting a blend of two or more ethylenically unsaturated acids or salts thereof with one substantially saturated antimicrobial quaternary ammonium compound, or by contacting a blend of two or more substantially saturated antimicrobial quaternary ammonium compounds with a blend of 2 or more ethylenically unsaturated acids or salts thereof. Conversely, blends of the antimicrobial surface active agents may be prepared by contacting a blend of two or more ethylenically unsaturated acids or salts thereof, with one substantially saturated antimicrobial quaternary ammonium compound, or by contacting a blend of two or more ethylenically unsaturated acids or salts thereof, with a blend of two or more substantially saturated antimicrobial quaternary ammonium compounds. The antimicrobial polymerizable surface active agents useful in the present invention to form latexes, when used in a antimicrobial CASE material, such as for example, paint, printing ink, adhesive or pressure-sensitive adhesive, generally act as surfactants in the course of manufacture, storage or even processing thereof and, then, ceases to function as surfactants in due course thereafter. Furthermore, the antimicrobial polymerizable surfactants of the invention can be used not only as emulsifiers for emulsion polymerizations, but also as dispersing agents for suspension polymerization, dispersing agent for dyes and pigments, emulsifiers for waxes, finishing agents for fibers, emulsifier-dispersants for agrochemicals, antistatic agents for synthetic resins, and so on. In these and other applications, the aforementioned adverse effect of a residual traditional surfactant can be drastically reduced and/or eliminated.

These and other objects and advantages, as well as the scope, nature, and utilization of the claimed invention will become apparent to those skilled in the art from the following detailed description and claims.

BRIEF DESCRIPTION OF THE DRAWINGS

FIG. I is a partial 1 H NMR spectrum, showing the region of d 5.0–8.0, of the allylamine salt of dodecylbenzenesulfonic acid (ADDBS).

FIG. II is a partial 1 H NMR spectrum, showing the region of d 5.0–8.0, of a latex formulation.

DETAILED DESCRIPTION OF THE INVENTION

A method is provided for forming discrete polymer particles and latexes useful for preparing antimicrobial CASE materials, utilizing polymerizable surface active agents, wherein the method comprises: (1) preparing a mixture comprising at least one ethylenically unsaturated monomer and at least one antimicrobial polymerizable surface active agent; (2) polymerizing the mixture to form discrete polymer particles or a latex; and (3) formulating the polymer particles or latex into a antimicrobial CASE material. Typically, the formulating step involves the addition of various optional ingredients as detailed herein, to produce a final CASE product. Generally, these optional ingredients may be added before, during or preferably after the formation of the polymer particles or latex. Generally, any ethylenically unsaturated monomer that is capable of undergoing polymerization may be utilized in the present invention. The method of the present invention is particularly well suited to emulsion polymerization but may also be conducted as a solution polymerization, suspension polymerization, micro emulsion polymerization or inverse emulsion polymerization. The polymerization may be conducted in any manner known to the art, including but not limited to, free-radical initiated polymerization, thermal initiated polymerization and redox initiated polymerization using, for example, batch, continuous, or controlled monomer feed processes, known conditions of stirring time and temperature, and known kinds of additives such as initiators, surfactants, electrolytes, pH adjusting agents, buffering agents, protective colloids and the like. In general, the polymerization process of the present invention will be carried out from about 20° C. to about 120° C. (e.g., between about 50° C. and about 110° C.). These polymerization temperatures will vary with respect to the reactivity and concentration of the polymerization initiator being used. Batch polymerization times may vary depending on the method of polymerization and the monomers being polymerized. Such times may vary from about 10 minutes to about 10 hours. In general, the mixture may be a solution, emulsion, suspension or dispersion of the ethylenically unsaturated monomer and the polymerizable surface active agent. Further, the polymerizable surface active agent may be provided to the mixture as an aqueous solution.

In accordance with the present invention, polymerization may occur simultaneously as the mixture is being formed (i.e. as the monomer and the antimicrobial polymerizable surface active agent come in contact, a self-initiating polymerization occurs). Accordingly, the present invention also encompasses a method for continuous polymerization, utilizing at least one ethylenically unsaturated monomer and at least one antimicrobial polymerizable surface active agent.

The antimicrobial polymerizable surface active agents utilized in the present invention are quaternary ammonium compounds derived from:

a) at least one acid, wherein the acid is a sulfonic acid, a carboxylic acid, or a phosphoric acid, or a salt thereof, or a mixture thereof, wherein the acid or salt thereof contains at least one ethylenically unsaturated moiety; and b) at least one substantially saturated antimicrobial quaternary ammonium compound.

By substantially saturated antimicrobial quaternary ammonium compound, it is generally meant that the antimicrobial quaternary ammonium compound contains less than about 10% unsaturation in the alkyl group(s) and/or other functionalities. The antimicrobial polymerizable surface active agents are generally capable of polymerization with themselves, polymerization with the ethylenically unsaturated monomer or co-polymerization with a partially polymerized polymer particle. In a somewhat preferred embodiment, the antimicrobial polymerizable surface active agent is partially (i.e. 0.5–50 percent by weight of the polymerizable surface active agent) consumed by polymerization with itself, co-polymerization with the monomer and/or co-polymerization with a partially polymerized polymer particle. In a more preferred embodiment, the antimicrobial polymerizable, surface active agent is substantially (i.e. 50–90 percent by weight of the polymerizable surface active agent) consumed by polymerization with itself, co-polymerization with the monomer and/or co-polymerization with a partially polymerized polymer particle. In a most preferred embodiment, the antimicrobial polymerizable, surface active agent is substantially completely (i.e. greater than 90 percent by weight of the polymerizable surface active agent) consumed by polymerization with itself, co-polymerization with the monomer and/or co-polymerization with a partially polymerized polymer particle.

The antimicrobial polymerizable surface active agent and the ethylenically unsaturated monomer are in a ratio of about 0.01:1 to about 3:1 on a weight basis, prior to polymerization. In a preferred embodiment, the antimicrobial polymerizable surface active agent is present in the mixture in a concentration of about 0.1–100 weight percent, based on the total weight of the ethylenically unsaturated monomer present in the mixture. In a more preferred embodiment, the antimicrobial polymerizable surface active agent is present in the mixture in a concentration of about 1–20 weight percent, based on the total weight of the ethylenically unsaturated monomer present in the mixture. In another embodiment, the antimicrobial polymerizable surface active agent comprises about 0.1–10 weight percent of the polymer, more preferably 0.5–3.0, based on the total weight of the ethylenically unsaturated monomer present prior to polymerization.

In general, the method of preparing antimicrobial polymers and CASE materials in accordance with the present invention does not require the use of a non-polymerizable surfactant, i.e. the materials are substantially free of non-polymerizable, surface active agents. However, in a less preferred embodiment, the materials may further comprises a supplemental, non-polymerizable surfactant (iii); wherein the supplemental traditional surfactant is a sodium, potassium, calcium, magnesium, amine, or ammonium salt, or a mixture thereof, of a substantially saturated anionic surfactant, or a nonionic, cationic, or amphoteric surfactant, or a mixture thereof; and wherein the supplemental surfactant is provided in a concentration of about 0.01 to about 20.0 percent by weight, based on the total weight of polymerizable surface active agent and supplemental surfactant provided in the reaction zone.

The present invention provides pre-polymerization mixtures, useful in the preparation of antimicrobial CASE materials, comprising (1) at least one ethylenically unsaturated monomer; and (2) at least one antimicrobial polymerizable surface active agent; wherein the ethylenically unsaturated monomer and the antimicrobial polymerizable surface active agent are defined as above or below. This pre-polymerization mixture may be polymerized by a variety of initiation methods known to the art.

The present invention provides polymers useful in preparing antimicrobial CASE materials comprising an antimicrobial latex comprising: (1) at least one monomer unit; and (2) at least one surface active agent unit; wherein the monomer unit is derived from an ethylenically unsaturated monomer; wherein the surface active agent is derived from an antimicrobial polymerizable surface active agent; and wherein the ethylenically unsaturated monomer and the polymerizable surface active agent have co-polymerized to form the polymer.

In another embodiment, the present invention provides a method for forming antimicrobial CASE materials, wherein the method comprises (1) preparing a mixture comprising at least one ethylenically unsaturated monomer at least one acid, wherein the acid is a sulfonic acid, a carboxylic acid, or a phosphoric acid, or a salt thereof, or a mixture thereof, wherein the acid or salt thereof contains at least one ethylenically unsaturated moiety; and at least one substantially saturated antimicrobial quaternary ammonium compound; (2) polymerizing the mixture to form discrete polymer particles or a latex; and (3) formulating the polymer particles or latex into an antimicrobial CASE material. Typically, the formulating step involves the addition of various optional ingredients as detailed herein, to produce a final antimicrobial CASE product. In accordance with this embodiment, the acid or salt thereof, and the substantially saturated antimicrobial quaternary ammonium compound may form an antimicrobial polymerizable, surface active agent in situ; wherein the antimicrobial polymerizable surface active agent is capable of polymerization with itself, co-polymerization with the ethylenically unsaturated monomer and/or co-polymerizing with a partially polymerized polymer particle; and wherein the polymerizable, surface active agent is substantially completely consumed by polymerization with itself, co-polymerization with the monomer and/or co-polymerization with a partially polymerized polymer particle. In one alternative, the ethylenically unsaturated acid or a salt thereof may partially or completely co-polymerize with the ethylenically unsaturated monomer, followed by formation of a polymerizable surface active agent (i.e. quateranary ammonium compound formation). Without being bound by any particular theory, it is believed that the ethylenically unsaturated acid or a salt thereof is incorporated into the polymer back-bone and the acid or salt, followed by subsequent quaternary ammonium compound formation, thereby adhering to the polymer. In another alternative within the purview of this embodiment, a portion of the substantially the ethylenically unsaturated acid or a salt thereof may polymerize with itself, co-polymerize with the ethylenically unsaturated monomer or co-polymerize with a partially polymerized polymer, followed by quaternary ammonium compound formation. In another alternative, the ethylenically unsaturated acid or a salt thereof may partially or completely co-polymerize with a homopolymeric surfactant, followed by quaternary ammonium compound formation.

The present invention provides antimicrobial CASE materials comprising: (1) at least one monomer unit; (2) at least one acid, wherein the acid is a sulfonic acid, a carboxylic acid, or a phosphoric acid, or a salt thereof, or a mixture thereof, wherein the acid or salt thereof contains at least one ethylenically unsaturated moiety; and at least one substantially saturated antimicrobial quaternary ammonium compound; wherein the monomer unit is derived from an ethylenically unsaturated monomer; wherein the acid or salt thereof is homopolymerized, co-polymerized with the monomer, and/or co-polymerized with a partially polymerized polymer, wherein thereafter the acid reacts with the substantially saturated antimicrobial quaternary ammonium compound to form an antimicrobial polymer.

In another embodiment, the present invention provides a method for forming antimicrobial CASE materials wherein the method comprises: (1) preparing a mixture comprising at least one ethylenically unsaturated monomer and at least one antimicrobial homopolymeric surface active agent, the homopolymeric surface active agent being a polymer formed by polymerizing at least one antimicrobial polymerizable, surface active agent as disclosed herein; (2) polymerizing the mixture to form discrete polymer particles or a latex; and (3) formulating the polymer particles or latex into an antimicrobial CASE material. Typically, the formulating step involves the addition of various optional ingredients as detailed herein, to produce a final antimicrobial CASE product.

The present invention relates to antimicrobial CASE materials comprising polymer latexes, wherein the polymer latex is based on polymers derived from at least one monomer and at least one antimicrobial polymerizable surface active agent of the instant invention.

The present invention provides antimicrobial homopolymeric surface active agents. These antimicrobial homopolymeric surface active agents are formed by polymerizing at least one antimicrobial polymerizable, surface active agent, wherein the antimicrobial polymerizable, surface active agent is a an polymerizable antimicrobial quaternary ammonium compound detailed herein. Optionally, the homopolymeric surface active agents may be formed by partially or completely polymerizing the ethylenically unsaturated acid, followed by complexation of the resulting polymer with the antimicrobial quaternary ammonium compound, wherein the acid and antimicrobial quaternary ammonium compound form an antimicrobial homopolymeric surface active agent.

The antimicrobial homopolymeric surface active agents of the invention are generally capable of polymerization with themselves, co-polymerization with the monomer or co-polymerization with a partially polymerized polymer.

In another embodiment, the present invention provides a method for antimicrobial CASE materials, wherein the method comprises: (1) partially polymerizing at least one ethylenically unsaturated monomer to form a partially polymerized polymer/monomer mixture; (2) adding to the partially polymerized polymer/monomer mixture at least one antimicrobial polymerizable surface active agent and/or at least one antimicrobial homopolymeric surface active agent detailed herein, to form a partially polymerized antimicrobial polymer/monomer/surface active agent mixture; (3) polymerizing the partially polymerized antimicrobial polymer/monomer/surface active agent mixture to form discrete polymer particles or a latex; and (4) formulating the polymer particles or latex into an antimicrobial CASE material; wherein the antimicrobial homopolymeric surface active agent being a surfactant formed by polymerizing at least one antimicrobial polymerizable, surface active agent detailed herein. Typically, the formulating step involves the addition of various optional ingredients as detailed herein, to produce a final CASE product.

In another embodiment, the present invention provides a method for forming antimicrobial CASE materials, wherein the method comprises: (1) preparing a mixture comprising at least one ethylenically unsaturated monomer and at least one non-polymerizable, supplemental surface active agent; (2) partially polymerizing the mixture to form a partially polymerized polymer/monomer/supplemental surface active agent mixture; (3) adding to the partially polymerized polymer/monomer/supplemental surface active agent mixture at least one antimicrobial polymerizable surface active agent and/or at least one antimicrobial homopolymeric surface active agent as described herein, to form a partially polymerized polymer/monomer/supplemental surface active agent/polymerizable surface active agent mixture; and (4) polymerizing the partially polymerized polymer/monomer/ surface active agent/polymerizable surface active agent mixture to form discrete polymer particle or a latex; and (5) formulating the polymer particles or latex into an antimicrobial CASE material. Typically, the formulating step involves the addition of various optional ingredients as detailed herein, to produce a final CASE product.

In another embodiment, the present invention provides a method for forming antimicrobial CASE materials, wherein the method comprises: (1) preparing a mixture comprising at least one ethylenically unsaturated monomer and at least one non-polymerizable, supplemental surface active agent; (2) partially polymerizing the mixture to form a polymer mixture; and (3) adding at least one antimicrobial polymerizable surface active agent and/or at least one antimicrobial homopolymeric surface active agent as detailed herein, to the polymer mixture; (4) polymerizing the mixture to substantial completion to form discrete polymer particles or a latex; (5) formulating the polymer particles or latex into an antimicrobial CASE material. Typically, the formulating step involves the addition of various optional ingredients as detailed herein, to produce a final CASE product.

The present invention encompasses antimicrobial polymers prepared by any of the methods or processes described herein. Generally, the methods of the present invention encompass, emulsions, suspensions or dispersion of polymers obtained therefrom.

The present invention includes articles of manufacture, the surfaces of which possess antimicrobial properties, comprising
A) a substrate; and
B) an antimicrobial coating, adhesive, sealant or elastomer; wherein the substrate is selected from the group consisting essentially of wood, metal, plastic, glass, ceramics, fiberglass, composite materials, cardboard, corrugated board, paper, textiles, non-woven materials, foam, tape or a combination thereof.; and wherein the coating, adhesive, sealant or elastomeric material comprises an antimicrobial polymer latex comprising:
 a) at least one monomer unit; and
 b) at least one surface active agent unit;
wherein the monomer unit is derived from an ethylenically unsaturated monomer; wherein the surface active agent is derived from an antimicrobial polymerizable surface active agent in the form of an antimicrobial quaternary ammonium compound comprising:
  i) at least one acid, wherein the acid is a sulfonic acid, a carboxylic acid, or a phosphoric acid, or a salt thereof, or a mixture thereof, wherein the acid or salt thereof contains at least one ethylenically unsaturated moiety; and
  ii) at least one substantially saturated antimicrobial quaternary ammonium compound;
and wherein the ethylenically unsaturated monomer and the antimicrobial polymerizable surface active agent have polymerized to form the polymer. The antimicrobial CASE material generally imparts sustained antimicrobial activity to the surface of the substrate. Additionally, the coating, adhesive, sealant or elastomeric material comprises optional formulation ingredients described herein.

This invention relates to a method for providing antimicrobial waterborne coating compositions. A "waterborne coating composition" herein is defined as a composition containing at least one pigment and at least one polymer latex dispersed in an evaporable medium which is predominantly composed of water. The antimicrobial polymer latex comprises a) at least one monomer unit; and
 b) at least one polymerizable surface active agent unit;
wherein the monomer unit is derived from an ethylenically unsaturated monomer; wherein the polymerizable surface active agent is derived from an antimicrobial polymerizable surface active agent in the form of an antimicrobial quaternary ammonium compound comprising:
  i) at least one acid, wherein the acid is a sulfonic acid, a carboxylic acid, or a phosphoric acid, or a salt thereof, or a mixture thereof, wherein the acid or salt thereof contains at least one ethylenically unsaturated moiety;
  ii) and at least one substantially saturated antimicrobial quaternary ammonium compound.;
and wherein the ethylenically unsaturated monomer and the antimicrobial polymerizable surface active agent have polymerized to form the polymer. The evaporable medium may contain, in addition to water, at least one water-miscible solvent such as, for example, isopropanol, propylene glycol, ethylene glycol methyl ether, ethylene glycol butyl ether, and propylene glycol propyl ether. The waterborne coating composition contains from 10% to 70%, by volume based on the volume of the coating composition, of at least one pigment. The pigment is selected from inorganic and organic pigments such as, for example, titanium dioxide, calcium carbonate, polystyrene particles, and void-containing polymeric particles on the basis of color and opacity. Included in the term "pigment" herein are inorganic pigments sometimes referred to as fillers such as, for example, clay. Preferred is titanium dioxide as a predominant pigment.

In another aspect of the present invention the polymer latex of the antimicrobial waterborne coating may be prepared by a multi-stage emulsion addition polymerization process, in which at least two stages differing in composition are polymerized in sequential fashion. Such a process usually results in the formation of at least two mutually incompatible polymer compositions, thereby resulting in the formation of at least two phases within the polymer particles. Such particles are composed of two or more phases of various geometries such as, for example, core/shell or core/sheath particles, core/shell particles with shell phases incompletely encapsulating the core, core/shell particles with a multiplicity of cores, and interpenetrating network particles, in all of these cases the majority of the surface area of the particle will be occupied by at least one outer phase and the interior of the particle will be occupied by at least one inner phase. Each of the stages of the multi-staged emulsion-polymerized polymer may contain the same monomers, polymerizable surface active agents, chain transfer agents, etc. as disclosed herein. The emulsion polymerization techniques used to prepare such dispersions are well known in the art such as, for example, U.S. Pat. Nos. 4,325,856; 4,654,397; and 4,814,373.

The antimicrobial waterborne coating composition is prepared by paint making techniques which are well known in the coatings art. First, at least one pigment is well dispersed in a waterborne medium under high shear such as is afforded by a COWLES® mixer. Then the emulsion-polymerized addition polymer is added under low shear stirring along with other coatings adjuvants as desired. The antimicrobial waterborne coating composition may contain, in addition to the pigment(s) and the latex polymer, conventional coatings adjuvants such as, for example, colloids, emulsifiers, coalescing agents, curing agents, thickeners, humectants, wetting agents, biocides, plasticizers, antifoaming agents, colorants, waxes, and antioxidants.

The antimicrobial waterborne coating composition may be applied to a surface such as, for example, metal, wood, and plastic, using conventional coating application methods such as, for example, brush, roller, drawdown, dipping, curtain coater, and spraying methods such as, for example, air-assisted spray, airless spray, high volume low pressure spray, and air-assisted electrostatic spray.

The invention additionally encompasses antimicrobial paint compositions, caulk compositions, adhesive compositions and sealant compositions, and methods of preparing such compositions.

The invention includes a latex paint composition comprising an antimicrobial latex prepared as described herein, a pigment, and, optionally, thickener.

Ethylenically Unsaturated Monomers

The ethylenically unsaturated monomer or monomers that may be polymerized or co-polymerized according to the present invention are known to the art and are described below in a representative manner. Examples of suitable ethylenically unsaturated monomers are, for example, mono- and polyunsaturated hydrocarbon monomers, vinyl esters (e.g., vinyl esters of $C_1$ to $C_6$ saturated monocarboxylic acids), vinyl ethers, monoethylenically unsaturated mono- and polycarboxylic acids and there alkyl esters (e.g., acrylic acid esters and methacrylic acid esters, particularly the $C_1$ to $C_{12}$ alkyl, and more particularly the $C_1$ to $C_4$ alkyl esters), the nitriles, vinyl and vinylidene halides, and amides of unsaturated carboxylic acids and amino monomers.

Examples of suitable hydrocarbon monomers for use in the present invention include styrene compounds (e.g., styrene, carboxylated styrene, and alpha-methyl styrene), ethylene, propylene, butylene, and conjugated dienes (e.g., butadiene, isoprene and copolymers of butadiene and isoprene). Examples of vinyl and vinylidene halides include vinyl chloride, vinylidene chloride, vinyl fluoride and vinylidene fluoride.

Examples of acrylic esters and methacrylic esters suitable for use in the present invention include $C_1$–$C_{12}$ (e.g., $C_1$–$C_4$) alkyl acrylates and methacrylates. Typical alkyl esters and methacrylic esters include methyl acrylate, methyl methacrylate, ethyl acrylate, ethyl methacrylate, isopropyl acrylate, isopropyl methacrylate, n-butyl acrylate, n-butyl methacrylate, isobutyl acrylate, isobutyl methacrylate, hexyl acrylate, 2-ethylhexyl acrylate, 2-ethylhexyl methacrylate, t-butyl acrylate, t-butyl methacrylate, 3,3-dimethylbutyl acrylate, 3,3-dimethyl butyl methacrylate, and lauryl acrylate.

Suitable vinyl esters for use in the present invention include aliphatic vinyl esters, such as vinyl formate, vinyl acetate, vinyl propionate, vinyl butyrate, vinyl isobutyrate, vinyl valerate, and vinyl caproate, and alkyl esters of saturated monocarboxylic acids, such as alkyl acetate, alkyl propionate and ally lactate.

Vinyl ethers suitable for use in the present invention include methylvinyl ether, ethylvinyl ether and n-butylvinyl ether. Typically vinyl ketones include methylvinyl ketone, ethylvinyl ketone and isobutylvinyl ketone. Suitable dialkyl esters of monoethylenically unsaturated dicarboxylic acids include dimethyl maleate, diethyl maleate, dibutyl maleate, dioctyl maleate, diisooctyl maleate, dinonyl maleate, diisodecyl maleate, ditridecyl maleate, dimethyl fumarate, diethyl fumarate, dipropyl fumarate, dibutyl fumarate, dioctyl fumarate, diisooctyl fumarate, didecyl fumarate, dimethyl itaconate, diethyl itaconate, dibutyl itaconate, and dioctyl itaconate.

Monoethylenically unsaturated monocarboxylic acids suitable for use in the present invention include acrylic acid, methacrylic acid, ethacrylic acid, and crotonic acid. Suitable monoethylenically unsaturated dicarboxylic acids include maleic acid, fumaric acid, itaconic acid and citraconic acid. Suitable monoethylenically unsaturated tricarboxylic acids include aconitic acid and the halogen-substituted derivatives (e.g., alphachloracylic acid), and the anhydrides of these acids (e.g., maleic anhydride and citraconic anhydride).

Nitriles of the above ethylenically unsaturated mono-, di- and tricarboxylic acids which are suitable monomers include acrylonitrile, alpha-chloroacrylonitrile and methacrylonitrile. Suitable amides of these carboxylic acids include unsubtituted amides such as acrylamide, methacrylamide and other alpha-substituted acrylamides and N-substituted amides obtained by the reaction of the amides of the aforementioned mono- and polycarboxylic acids with and aldehyde (e.g., formaldehyde). Typical N-substituted amides include N-methylolacrylamide, N-methylolmethacrylamide alkylated N-methylolacrylamides and N-methylolmethacrylamides (e.g., N-methyoxymethylacrylamide and N-methoxymethylmethacrylamide).

Amino monomers useful in the present invention include substituted and unsubstituted aminoalkyl acrylates, hydrochloride salts of amino monomers and methacrylates, such as beta-aminoethylacrylate, beta-amino-ethylmethacrylate, dimethylaminomethylacrylate, beta-methylaminoethylacrylate, and dimethylaminomethylmethacrylate.

Hydroxy-containing monomers useful in the present invention include beta-hydroxyethylacrylate, beta-hydroxypropylacrylate, gamma-hydroxypropylacrylate and beta-hydroxyethylmethacrylate.

Suitable cationic monomers are alpha, beta-ethylenically unsaturated compounds which can undergo polymerization and contain primary, secondary or tertiary amino groups, such as, for example, dimethylaminoethyl methacrylate, dimethylaminoneopentyl acrylate, dimethylaminopropyl methacrylate, tert-butylaminoethyl methacrylate and the like, or organic or inorganic salts thereof, and/or alkylammonium compounds, such as, for example, trimethylammonium-ethyl methacrylate chloride, beta-acetamidodiethylaminoethyl acrylate chloride, methacrylamidopropyltrimethylammonium chloride, diallyldimethylammonium chloride and the like. These cataionic monomers may be used alone or in combination with the afforementioned monomers, provided that such use is compatible with the emulsion polymerization process.

Monomers useful in the present invention may be homopolymerized or copolymerized, i.e., one or more different monomers capable of polymerization may be used.

Polymerizable Antimicrobial Surface Active Agents

The antimicrobial polymerizable surface active agents utilized in the present invention are polymerizable antimicrobial quaternary ammonium compounds derived from at least one acid, wherein the acid is a sulfonic acid, a carboxylic acid, or a phosphoric acid, or a salt thereof, or a mixture thereof, wherein the acid or salt thereof contains at least one ethylenically unsaturated moiety; and at least one substantially saturated antimicrobial quaternary ammonium compound. The antimicrobial polymerizable surface active agent is usually present in the mixture in a concentration from about 0.01–100.0 percent by weight based on the total weight of the ethylenically unsaturated monomer. In general, although not required, the antimicrobial polymerizable surface active agents have a hydrophilic/lipophilic balance (HLB) of less than about 45. In a somewhat more preferred embodiment, the polymerizable surface active agents have an HLB of about 5–40. The antimicrobial polymerizable surface active agents are generally capable of polymerization with themselves, co-polymerization with the ethylenically unsaturated monomer, or co-polymerization with a partially polymerized polymer.

The antimicrobial polymerizable surface active agents of the present invention are prepared from readily available, economical raw materials, and generally, their preparation does not require any special handling or equipment. The antimicrobial polymerizable surface active agents and blends of such agents may be prepared in a variety of forms such as, for example, liquids, solutions, solids, powders, flakes, semi-solids, gels, "ringing" gels, G-phase liquids, hexagonal phase solids, or thick pastes. These agents may be spray dried, flaked, extruded, and the like. Although not critical to the present invention, the antimicrobial polymerizable surface active agents may be prepared "neat" or in a conventional solvent such as water, low molecular weight alcohol or hydrocarbon, or a mixture thereof, to produce a solution of the polymerizable surface active agent. The present invention encompasses antimicrobial polymerizable surface active agents in dry form and as aqueous/solvent solutions. These agents may be isolated by drying a solution of the surface active agents; a solution of agents may be prepared by dissolving a solid form of the agent in water, low molecular weight alcohol or hydrocarbon, or a mixture thereof. Antimicrobial polymerizable surface active agents of the present invention may be prepared to produce a surface active mixture comprising "neat" surface active agents or an aqueous surfactant blend.

The antimicrobial polymerizable surface active agents utilized in the present invention may be homopolymerized (i.e. polymerized with themselves), or partially homopolymerized, prior to use in the polymerization, to form an antimicrobial homopolymeric surface active agent or a blend of homopolymeric surface active agent(s) and polymerizable surface active agents.

Ethylenically Unsaturated Acids and Salts Thereof

In general, the ethylenically unsaturated acids or salts thereof, which are useful in the present invention are any sulfonic acids, carboxylic acids, or phosphoric acids or salts thereof which contain at least one ethylenically unsaturated moiety. More specifically, the ethylenically unsaturated acids useful in the present invention are generally vinyl sulfonic acids, vinyl sulfinic acids, vinyl sulfenic acids, vinyl sulfonic acid esters, vinyl carboxylic acids, vinyl phosphoric acids, vinyl phosphonic acids, vinyl phosphinic, vinyl phosphenic acids, unsaturated, e.g., alkyl sulfonic acids, unsaturated polysulfonic acids, unsaturated sulfonic acids of oils, unsaturated paraffin sulfonic acids, unsaturated lignin sulfonic acids, unsaturated petroleum sulfonic acids, unsaturated tall oil acids, olefin sulfonic acids, unsaturated hydroxyolefin sulfonic acids, unsaturated polyolefin sulfonic acids, unsaturated polyhydroxy polyolefin sulfonic acids, unsaturated carboxylic acids, unsaturated perfluorinated carboxylic acids, unsaturated carboxylic acid sulfonates, unsaturated alkoxylated carboxylic acid sulfonic acids, unsaturated polycarboxylic acids, unsaturated polycarboxylic acid polysulfonic acids, unsaturated alkoxylated polycarboxylic acid polysulfonic acids, unsaturated phosphoric acids, unsaturated alkoxylated phosphoric acids, unsaturated polyphosphoric acids, and unsaturated alkoxylated polyphosphoric acids, unsaturated fluorinated phosphoric acids, unsaturated phosphoric acid esters of oils, unsaturated phosphinic acids, unsaturated alkylphosphinic acids, unsaturated aminophosphinic acids, unsaturated polyphosphinic acids, unsaturated vinyl phosphinic acids, unsaturated phosphoric acids, unsaturated polyphosphonic acids, unsaturated phosphoric acid alkyl esters, unsaturated α-phosphono fatty acids, unsaturated oragnoamine polymethylphosphonic acids, unsaturated organoamino dialkylene phosphoric acids, unsaturated alkanolamine phosphoric acids, unsaturated trialkyledine phosphoric acids, unsaturated acylamidomethane phosphoric acids, unsaturated alkyliminodimethylene diphosphonic acids, unsaturated polyethylene-bis(nitrilodimethylene)tetraphosphonic acids, unsaturated alkyl bis(phosphonoalkylidene) amine oxide acids, unsaturated esters of substituted aminomethylphosphonic acids, unsaturated phosphonamidic acids, unsaturated acylated amino acids (e.g., amino acids reacted with alkyl acyl chlorides, alkyl esters or carboxylic acids to produce N-acylamino acids), unsaturated N-alkyl acylamino acids, and unsaturated acylated protein hydrolysates, and salts thereof, and mixtures thereof.

Other ethylenically unsaturated acids and salts thereof which are useful in the present invention are selected from the group comprising unsaturated linear or branched alkylbenzene sulfonic acids, unsaturated alkyl sulfuric acid esters, unsaturated alkoxylated alkyl sulfuric acid esters, unsaturated α-sulfonated alkyl ester acids, unsaturated α-sulfonated ester diacids, unsaturated alkoxylated α-sulfonated alkyl ester acids, unsaturated α-sulfonated dialkyl diester acids, unsaturated di-α-sulfonated dialkyl diester acids, unsaturated α-sulfonated alkyl acetate acids, unsaturated primary and secondary alkyl sulfonic acids, unsaturated perfluorinated alkyl sulfonic acids, unsaturated sulfosuccinic mono- and diester acids, unsaturated polysulfosuccinic polyester acids, unsaturated sulfoitaconic diester acids, unsaturated sulfosuccinic acids, unsaturated sulfosuccinic amide acids, unsaturated sulfosuccinic imide acids, unsaturated phthalic acids, unsaturated sulfophthalic acids, unsaturated sulfoisophthalic acids, unsaturated phthalamic acids, unsaturated sulfophthalic acids, unsaturated alkyl ketone sulfonic acids, unsaturated hydroxyalkane-1-sulfonic acids, unsaturated lactone sulfonic acids, unsaturated sulfonic acid amides, unsaturated sulfonic acid diamides, unsaturated alkyl phenol sulfuric acid esters, unsaturated alkoxylated alkyl phenol sulfuric acid esters, unsaturated alkylated cycloalkyl sulfuric acid esters, unsaturated alkoxylated alkylated cycloalkyl sulfuric acid esters, unsaturated dendritic polysulfonic acids, unsaturated dendritic polycarboxylic acids, unsaturated dendritic polyphosphoric acids, unsaturated sarcosinic acids, unsaturated isethionic acids, and unsaturated tauric acids, and salts thereof, and mixtures thereof.

Additionally in accordance with the present invention, suitable ethylenically unsaturated acids and salts thereof of the present invention include unsaturated fluorinated carboxylic acids, unsaturated fluorinated sulfonic acids, unsaturated fluorinated sulfate acids, unsaturated fluorinated phosphoric and phosphinic acids, and salts thereof and mixtures thereof.

Other ethylenically unsaturated acids or salts thereof suitable for use in the invention are:

| | |
|---|---|
| 3-Sulphoethylmethacrylate | methallylsulfonate |
| allylsulfonate | 3-sulfopropylacrylate |
| 3-sulfoethylacrylate | sulfomethacrylate |

| -continued | |
|---|---|
| ethylsulfonate monodecylmaleate | fumaric acid derivatives |
| styrene sulfonates | 2-acrylamido-2-methylpropanesulfonic acid |
| Tetrallylortho silicate | Triallyl citrate |
| Triallyl phosphate | Triallyl trimellitate |

Antimicrobial Quaternary Ammonium Compounds

In general, the antimicrobial quaternary ammonium compounds of the present invention are those which are capable of forming a polymerizable antimicrobial quaternary ammonium compound by combination with the ethylenically unsaturated acids of the invention. The antimicrobial quaternary ammonium compounds suitable for use in the present invention include those disclosed in U.S. Pat. Nos. 4,444,790, 5,049,383, 4,450,174, and 5,444,094, the disclosure of each of which is incorporated herein by reference in its entirety.

The antimicrobial quaternary ammonium compounds useful in the invention have the following general formula:

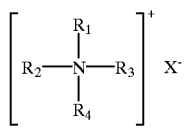

wherein $R_1$ and $R_2$ are straight or branched chain lower alkyl groups having from one to seven carbon atoms; $R_3$ is a straight or branched chain higher alkyl group having from about eight to twenty carbon atoms, or a benzyl group; $R_4$ is a straight or branched chain higher alkyl group having from about eight to twenty carbon atoms; and X is a halogen or a methosulfate or saccharinate ion.

In preferred quaternary ammonium salts of Formula I, $R_1$ and $R_2$ are methyl groups; $R_3$ is benzyl or straight or branched chain alkyl having from about eight to eighteen carbon atoms; and $R_4$ is straight or branched chain alkyl having from about eight to eighteen carbon atoms. A preferred halogen is chlorine, or a methosulfate or a saccharinate ion.

Illustrative of suitable quaternary ammonium germicides for use in the invention are: dioctyl dimethyl ammonium chloride, octyl decyl dimethyl ammonium chloride, didecyl dimethyl ammonium chloride, (C12–C18) n-alkyl dimethyl benzyl ammonium chloride, (C12–C18) n-alkyl dimethyl ethylbenzyl ammonium chloride, (C12–C18) n-alkyl dimethyl benzyl ammonium saccharinate, and didecyl alkyl dimethylammonium chloride in which the decyl radical is a mixture of primary 10-carbon atom branched chains. This is not an exhaustive list and other quaternary ammonium salts having germicidal activity will suffice.

The quaternary ammonium salt in the present invention need not be a single entity, but may be a blend of two or more quaternary ammonium salts. The amount, in weight-percent, of the quaternary ammonium salt, either as a single entity or blended, is typically from about 0.1%–2.0%. The preferred quaternary ammonium germicide is a mixture of about 34% by weight C12 and 16% by weight C14 n-alkyl dimethyl ethylbenzyl ammonium chloride and about 30% by weight C14, 15% by weight C16, 2.5% by weight C12 and 2.5% by weight C18 n-alkyl dimethyl benzyl ammonium chloride.

A representative antimicrobial quaternary ammonium compound is BTC® 2125 M which is a mixture of quaternary ammonium salts consisting of: 34% by weight $C_{12}$ and 16% by weight $C_{14}$ n-alkyl dimethyl ethylbenzyl ammonium chloride and about 30% by weight $C_{14}$, 15% by weight $C_{16}$, 2.5% by weight $C_{12}$ and 2.5% by weight $C_{18}$ n-alkyl dimethyl benzyl ammonium chloride, commercially available from Stepan Company, Northfield, Ill.

Additional representative antimicrobial quaternary ammonium compounds useful in the invention have the following formulas:

$R_1 = (C_8–C_{18})$-alkyl or -alkenyl, preferably -alkyl,
$R_2 = (C_8–C_{18})$-alkyl or -alkenyl, preferably -alkyl, aryl or $(C_7–C_{18})$-aralkyl, in which the aromatic rings can additionally be substituted, preferably by chlorine and/or bromine,
$R_3 = (C_1–C_4)$-alkyl, preferably methyl, or the radical $—(CH_2—CHR_4O)_n—R_5$, in which n denotes a number from 1 to 20 and $R_4$ and $R_5$, which can be identical or different, denote H and/or $(C_1–C_4)$-alkyl, $R_4$ preferably denoting H or methyl and R5 preferably denoting H, and
A=an anion of an organic or inorganic acid. Possible anions A are, for example, chloride, bromide, acetate, propionate, benzoate or 1 equivalent of sulfate.

The radicals $R_1$ and $R_2$ in formula (I) can be identical or different. Those surfactant compounds of the formula (I) in which at least one of the radicals $R_1$ and $R_2$ stands for $(C_{10}–C_{12})$-alkyl or both radicals $R_1$ and $R_2$ denote $(C_{10}–C_{12})$-alkyl exhibit a particular biocidal activity. Compounds of the formula (I) and (II) are, for example, octyl-trimethylammonium bromide, decyl-trimethyl-ammonium chloride, didecyl-dimethylammonium chloride, dedecyl-methylhydroxyethylammonium propionate, lauryl-trimethylammonium chloride, lauryl-pyridinium chloride, hexadecyl-trimethylammonium chloride, stearyl-trimethylammonium chloride and stearyl-dimethylbenzylammonium chloride.

Other examples of antimicrobial quaternary ammonium compounds suitable for use herein are:

Di($C_{8–10}$)alkyl dimethyl ammonium salts

Dicetyl dimethyl ammonium salts

Diisocetyl dimethyl ammonium salts

Polymeric quaternary ammonium salts such as Onamer® M.

Polymeric cationic microbiocides:
poly {oxyethylene(dimethylimino)ethylene (dimethylimino)ethylene salts Ethyoxyethyldiisobutylphenoxydimethyl benzylammonium salts Secondary Polymerizable Surfactants In accordance with the present invention, secondary polymerizable surface active agents may be used in the present invention. These secondary polymerizable surfactants are optionally present in about 0–10% by weight, based on the total weight of the monomer. The secondary polymerizable surfactant is typically in the form of an amine salt or quaternary ammonium compound comprising at least one substantially saturated acid, wherein the acid is a sulfonic acid, sulfuric acid ester, carboxylic acid, or phosphoric acid, or a mixture thereof; and at least one nitrogenous base, wherein the nitrogenous base contains at least one nitrogen atom and at least one ethylenically unsaturated moiety.

The acids useful in forming the secondary polymerizable surfactants of the present invention are generally sulfonic acids, polysulfonic acids, sulfonic acids of oils, paraffin sulfonic acids, lignin sulfonic acids, petroleum sulfonic acids, tall oil acids, olefin sulfonic acids, hydroxyolefin sulfonic acids, polyolefin sulfonic acids, polyhydroxy polyolefin sulfonic acids, carboxylic acids, perfluorinated carboxylic acids, carboxylic acid sulfonates, alkoxylated carboxylic acid sulfonic acids, polycarboxylic acids, polycarboxylic acid polysulfonic acids, alkoxylated polycarboxylic acid polysulfonic acids, phosphoric acids, alkoxylated phosphoric acids, polyphosphoric acids, and alkoxylated polyphosphoric acids, fluorinated phosphoric acids, phosphoric acid esters of oils, phosphinic acids, alkylphosphinic acids, aminophosphinic acids, polyphosphinic acids, vinyl phosphinic acids, phosphoric acids, polyphosphonic acids, phosphoric acid alkyl esters, α-phosphono fatty acids, oragnoamine polymethylphosphonic acids, organoamino dialkylene phosphoric acids, alkanolamine phosphoric acids, trialkyledine phosphoric acids, acylamidomethane phosphoric acids, alkyliminodimethylene diphosphonic acids, polyethylene-bis(nitrilo dimethylene)tetraphosphonic acids, alkyl bis(phosphonoalkylidene) amine oxide acids, esters of substituted aminomethylphosphonic acids, phosphonamidic acids, acylated amino acids (e.g., amino acids reacted with alkyl acyl chlorides, alkyl esters or carboxylic acids to produce N-acylamino acids), N-alkyl acylamino acids, and acylated protein hydrolysates, and mixtures thereof.

Other acids which are useful in forming the secondary polymerizable surfactants of the present invention are selected from the group comprising linear or branched alkylbenzene sulfonic acids, alkyl sulfuric acid esters, alkoxylated alkyl sulfuric acid esters, α-sulfonated alkyl ester acids, α-sulfonated ester diacids, alkoxylated α-sulfonated alkyl ester acids, α-sulfonated dialkyl diester acids, di-α-sulfonated dialkyl diester acids, α-sulfonated alkyl acetate acids, primary and secondary alkyl sulfonic acids, perfluorinated alkyl sulfonic acids, sulfosuccinic mono- and diester acids, polysulfosuccinic polyester acids, sulfoitaconic diester acids, sulfosuccinic acids, sulfosuccinic amide acids, sulfosuccinic imide acids, phthalic acids, sulfophthalic acids, sulfoisophthalic acids, phthalamic acids, sulfophthalic acids, alkyl ketone sulfonic acids, hydroxyalkane-1-sulfonic acids, lactone sulfonic acids, sulfonic acid amides, sulfonic acid diamides, alkyl phenol sulfuric acid esters, alkoxylated alkyl phenol sulfuric acid esters, alkylated cycloalkyl sulfuric acid esters, alkoxylated alkylated cycloalkyl sulfuric acid esters, dendritic polysulfonic acids, dendritic polycarboxylic acids, dendritic polyphosphoric acids, sarcosinic acids, isethionic acids, and tauric acids, and mixtures thereof.

Additionally in accordance with the present invention, suitable acids for use in forming the secondary polymerizable surfactants of the present invention include fluorinated carboxylic acids, fluorinated sulfonic acids, fluorinated sulfate acids, fluorinated phosphoric and phosphinic acids, and mixtures thereof.

Due to their inherent hydrolytic instability, the sulfuric acid esters are preferably immediately converted to ethylenically unsaturated amine salts. For example, linear dodecyl alcohol is sulfated with $SO_3$ to produce an intermediate, hydrolytically unstable, dodecyl alcohol sulfate acid as shown in Scheme I below. The intermediate acid is neutralized with an ethylenically unsaturated substantially saturated nitrogenous base, such as allyl amine, to produce a dodecyl sulfate ethylenically unsaturated amine salt.

Scheme I: Formation of Dodecyl Sulfate
Ethylenically Unsaturated Amine Salt

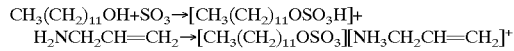

Additionally, for example, methyl laurate is sulfonated with $SO_3$ to produce an intermediate α-sulfonated lauryl methyl ester acid, as shown in Scheme II below. This acid is neutralized with an ethylenically unsaturated substantially saturated nitrogenous base, such as allyl amine, to produce an α-sulfonated lauryl methyl ester ethylenically unsaturated amine salt. Additionally, an α-sulfonated lauryl methyl ester ethylenically unsaturated amine di-salt may be produced as shown below in Scheme III. The α-sulfonated lauryl methyl ester ethylenically unsaturated amine salt and the α-sulfonated lauryl fatty acid ethylenically unsaturated amine di-salt may be formed as a mixture depending on the sulfonation conditions employed. The ratio of unsaturated amine salt to unsaturated amine di-salt is readily controlled by sulfonation conditions, well known to those skilled in the art.

Scheme II
Formation of α-Sulfonated Lauryl Methyl Ester Ethylenically Unsaturated Amine Salt

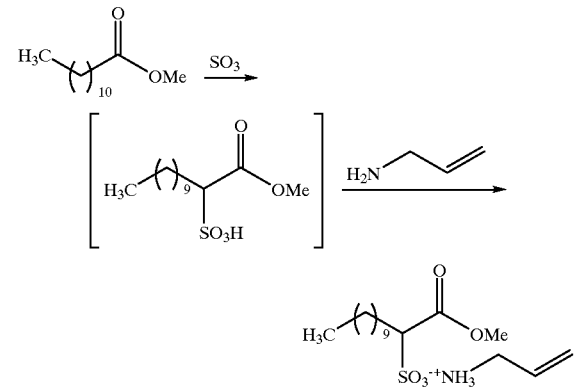

Scheme III
Formation of α-Sulfonated Lauryl Methyl Ester Ethylenically Unsaturated Amine Di-Salt

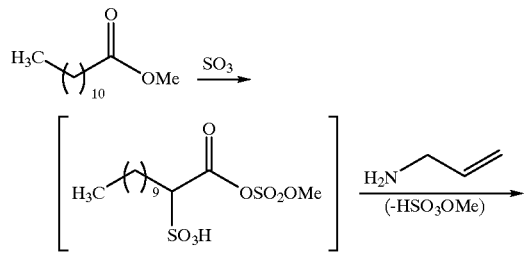

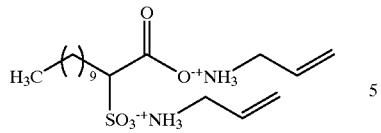

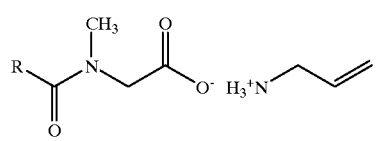

Ethylenically unsaturated amine salts of sulfosucinnate ester acids are typically produced by sulfitation of a succinic acid alkyl diester with sodium bisulfite, followed by, for example, ionic exchange with an ethylenically unsaturated substantially saturated nitrogenous base, such as allyl amine, as shown in Scheme IV below.

Scheme IV
Formation of a Sulfosuccinate Ester
Ethylenically Unsaturated Amine Salt

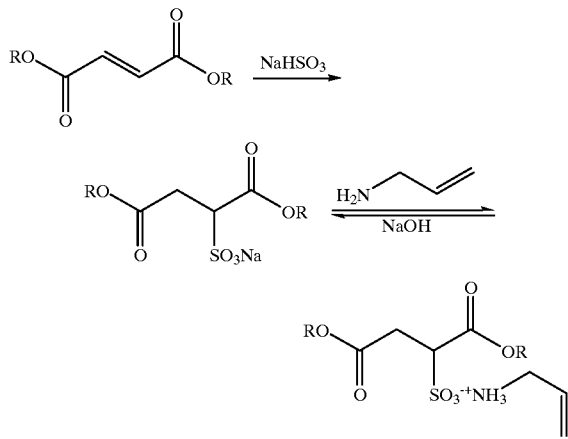

The sarcosinic acid ethylenically unsaturated amine salts are prepared by the amidation of a fatty acid, a fatty acid alkyl ester or a fatty acid chloride with sarcosine, followed by addition of an ethylenically unsaturated substantially saturated nitrogenous base, such as allyl amine, as shown in Scheme V below. Optionally, and somewhat less preferably, the ethylenically unsaturated substantially saturated nitrogenous base is combined with sarcosine to produce the corresponding sarcosine salt, which is then be used to amidate the fatty acid, fatty acid alkyl ester or fatty acid chloride.

Scheme V:
Formation Of A Fatty Sarcosinate Acid
Ethylenically Unsaturated Amine Salt

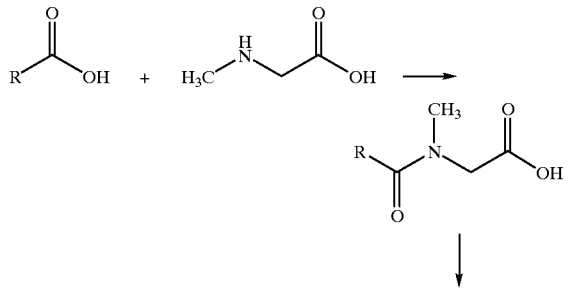

The isethionic acid ethylenically unsaturated amine salts may be prepared by the esterification of a fatty acid, a fatty acid alkyl ester or a fatty acid chloride with isethionic acid, followed by addition of an ethylenically unsaturated substantially saturated nitrogenous base, such as allyl amine, as shown in Scheme VI below. Additionally, isethionic acid ethylenically unsaturated amine salts may be prepared by esterifying a fatty acid, a fatty acid alkyl ester or a fatty acid chloride with the sodium salt of isethionic acid, followed by ion exchange with the ethylenically unsaturated substantially saturated nitrogenous base, such as allyl amine. Optionally, isethionic acid, or its sodium salt, may be combined with the ethylenically unsaturated substantially saturated nitrogenous base, such as allyl amine, to produce the allyl isethionic acid allyl amine salt, which may then be esterified with a fatty acid, a fatty acid alkyl ester or a fatty acid chloride.

Scheme VI:
Formation Of An Isethionic Acid
Ethylenically Unsaturated Amine Salt

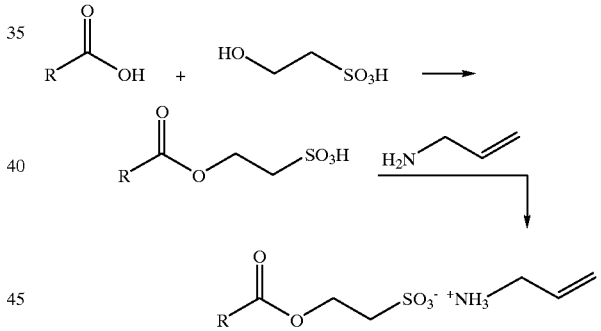

The preferred acids of the present invention are branched or linear alkylbenzene sulfonic acids, alkyl sulfuric acid esters, alkoxylated alkyl sulfuric acid esters, α-sulfonated alkyl ester acids, fatty carboxylic acids and phosphoric acid esters, and mixtures thereof. The most preferred acids of the present invention are branched or linear alkylbenzene sulfonic acids, alkyl sulfuric acid esters, and alkoxylated alkyl sulfuric acid esters, and mixtures thereof.

Other useful surfactants in accordance with the present invention include sulfonic acid salts of ethylenically unsaturated amines, derived from sultone precursors, such as cyclic alkyl sultones. Examples of these sultone-derived sulfonic acid salts (e.g., allyl amine salts) include 2-acetamidoalkyl-1-sulfonates and amino carboxy acid alkyl sulfonates, as shown in Scheme VII and Scheme VIII below.

Scheme VII:
2-Acetamidoalkyl-1-Sulfonic Acid Allyl Amine Salts

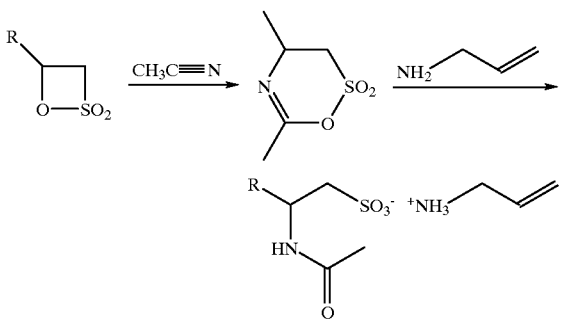

where R is $C_{4-24}$ alkyl.

Scheme VIII:
Amino Carboxy Acid Alkyl Sulfonic Acid Allyl Amine Salts

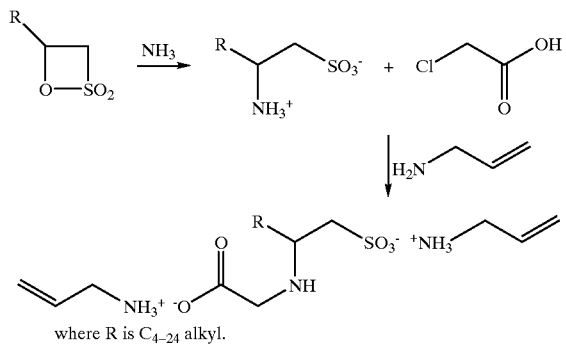

where R is $C_{4-24}$ alkyl.

In general, nitrogenous bases which are useful in the present invention in forming the secondary polymerizable surfactants are any substantially saturated nitrogenous base which contains an ethylenically unsaturated moiety, including various vinyl amines. The nitrogenous base useful in accordance with the present invention is a compound of the formula

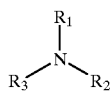

wherein $R_1$, $R_2$ and $R_3$ are independently hydrogen or organic groups containing an ethenylene group, provided that at least one of $R_1$–$R_3$ is a straight or branched chain alkyl group containing 1–8 carbon atoms and an ethenylene functionality.

Additionally, other examples of substantially saturated nitrogenous bases that are useful in forming the secondary polymerizable surfactants of the present invention are ethylenically unsaturated amines selected from the group comprising vinyl amine, N-methyl N-alkyl amine, $C_1$–$C_{24}$ alkyl allyl amine, $C_1$–$C_{24}$ alkyl ethoxylated and/or propoxylated alkyl amine, $C_1$–$C_{24}$ dialkyl allyl amine, ethoxylated and/or propoxylated allyl amine diallyl amine, $C_1$–$C_{24}$ alkyl diallyl amine, ethoxylated and/or propoxylated diallyl amine, triallyl amine, 1,2-diaminoethene, aminocrotonitrile, diaminomaleonitrile, N-allylcyclopentylamine, N-allylaniline, allylcyclohexylamine, [1-(2-allylphenoxy)-3-(isopropylamino)2-propanol], 3-amino-2-butenethioamide, bis[4-(dimethylamino)-benzylidene]acetone, 1,4-butanediol bis(3-aminocrotonate), 3-amino-1-propanol vinyl ether, 2-(diethylamino)ethanol vinyl ether, 4-(diethylamino)cinnamaldehyde, 4-(diethylamino)cinnamonitrile, 2-(diethylamino)ethyl methacrylate, diethyl (6-methyl-2-pyridylaminomethylene)maleate, 3-(dimethylamino)acrolein, 2-(dimethylamino)ethyl methacrylate, 4-dimethylaminocinnamaldehyde, 2-(dimethylamino)ethyl acrylate, 3-(dimethylamino)-2-methyl-2-propenal, 9-vinylcarbazole, N-vinylcaprolactam, 1-vinylimidazole, 2-vinylpyridine, 4-vinylpyridine, allylcyclohexylamine, N-allylcyclopentylamine, allyl (diisopropylamino)dimethylsilane, 1-allylimidazole, 1-vinyl-2-pyrrolidinone, N-[3-(dimethylamino)propyl]methacrylamide, 4-[4-(dimethylamino)styryl]pyridine, 2-[4-(dimethylamino)styryl]pyridine, 2-[4-(1,2-diphenyl-1-butenyl)phenoxy]—N,N-dimethylethylamine, 2-[4-dimethylamino)styryl]-benzothiozole, 5-[4-(dimethylamino)phenyl]-2,4-pentandienal, (dimethylaminomethylene)malononitrile, 4-dimethylaminocinnamonitrile, 4-(dimethylamino)chalcone, [6-(3,3-dimethylallylamino-purine riboside, 3,7-dimethyl-2,6-octadien-1-ylamine, 2-isopropenylaniline, isopropyl 3-aminocrotonate, S-{2-[3-(hexyloxy)benzoyl]-vinyl}glutathione, methyl 3-aminocrotonate, N-methylallylamine, N-methyl-1-(methylthio)-2-nitroetheneamine, oleylamine, tetrakis (dimethylamino)ethylene, 5-[(6,7,8-trimethoxy-4-quinazolinyl)amino]-1-pentanol nitrate ester, tris(2-methylallyl)amine, N,N,N',N'-tetramethyl-2-butene-1,4-diamine, S-{2-[3-(octyloxy)benzoyl]vinyl}-glutathione, 4,4'-vinylidene-(N,N-dimethylaniline), 2',5'-dimethoxy-4-stilbenamine, 3-(dimethylamino)propyl acrylate, 3-dimethylaminoacrylonitrile, 4-(dimethylamino)-cinnamic acid, 2-amino-1-propene-1,1,3-tricarbonitrile, 2-aminopentenoic acid, N,N'-diethyl-2-butene-1,4-diamine, 10,11-dihyro-N,N-dimethyl-5-methylene-5H-dibenzo[a,d]-cyclohepene-10-ethanamine maleate, 4-(dicyanomethylene)-2-methyl-6-(4-dimethylaminostyryl)-4H-pyran, N-ethyl-2-methylallylamine, ethyl 3-aminocrotonate, ethyl-α-cyano-3-indoleacrylate, ethyl-3-amino-4,4-dicyano-3-butenoate, 1,3-divinyl-1,1,3,3-tetramethyldisilazane, N-(4,5-dihydro-5-oxo-1-phenyl-1H-pyrazol-3-yl)-9-octadecen-amide, and N-oleoyl-tryptophan ethyl ester, and mixtures thereof.

More preferred nitrogenous bases useful in forming the secondary polymerizable surfactants of the present invention are allyl amine, diallyl amine, triallyl amine, methylallyl amine, N-allyl-N,N-dimethyl amine, methyl 3-amino crotonate, 3-amino crotononitrile, 3-amino-1-propanol vinyl ether, N-methyl N-allyl amine, 2-(dimethylamino)ethyl acrylate, or 1,4-diamino-2-butene, and mixtures thereof. The most preferred substantially saturated nitrogenous bases of the present invention are alkyl amine, diallyl amine, triallyl amine, methallyl amine, N-methyl N-alkyl amine, and 2-(dimethylamino)ethyl acrylate, and mixtures thereof.

Accordingly, the present invention may utilize secondary polymerizable surfactants of the formula:

wherein $R_1$ is a saturated or unsaturated hydrocarbon group having from about 1–24 carbon atoms; wherein Ar is a phenyl, polyphenyl, napthyl, polynapthyl, styryl, or polystyryl group, or a mixture thereof; wherein $M^+$ is a conjugate acid of the nitrogenous base; wherein n is an integer of from 1–5 and m is an integer of from 1–8; and wherein the total number of carbon atoms represented by $(R_1)_n$ is at least 5. In a preferred embodiment $R_1$ is a saturated or unsaturated hydrocarbon group having from about 6–24 carbon atoms, Ar is a phenyl, $M^+$ is a conjugate acid of the nitrogenous base, the nitrogenous base selected from the group consisting of allyl amine, diallyl amine, triallyl amine, methallyl amine, N-methyl N-allyl amine or 2-(dimethylamino)ethyl acrylate, and mixtures thereof and n is 1 and m is 1. In another embodiment, the secondary polymerizable surfactant is of the formula:

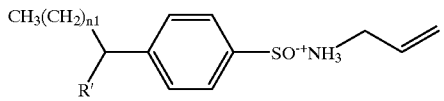

wherein n1=4–18; and wherein R' is hydrogen or saturated or unsaturated hydrocarbon group having from about 1–8 carbon atoms.

The present invention may utilize secondary polymerizable surfactants of the formula

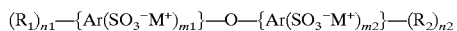

wherein $R_1$ and $R_2$ are independently hydrogen, or saturated or unsaturated hydrocarbon groups having from about 1–24 carbon atoms; wherein Ar is a phenyl, polyphenyl, napthyl, polynapthyl, styryl, or polystyryl group, or a mixture thereof; wherein $M^+$ is a conjugate acid of the substantially saturated nitrogenous base; wherein n1 and n2 are independently 0–5, provided that n1 and n2 are not both equal to zero; and wherein m1 and m2 are independently 0–8, provided that m1 and m2 are not both equal to zero. In a preferred embodiment, $R_1$ is hydrogen and $R_2$ is a saturated or unsaturated hydrocarbon group having from about 6–24 carbon atoms, Ar is phenyl, $M^+$ is a conjugate acid of the nitrogenous base, the nitrogenous base selected from the group consisting of allyl amine, diallyl amine, triallyl amine, methallyl amine, N-methyl N-allyl amine or 2-(dimethylamino)ethyl acrylate, and mixtures thereof, n1=4, n2=1, and m1 and m2 both equal one. In another embodiment, $R_1$ and $R_2$ are independently saturated or unsaturated hydrocarbon groups having from about 6–24 carbon atoms, Ar is phenyl, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, n1 and n2 both equal one, and m1 and m2 both equal one. In another embodiment, the secondary polymerizable surfactant is of the formula:

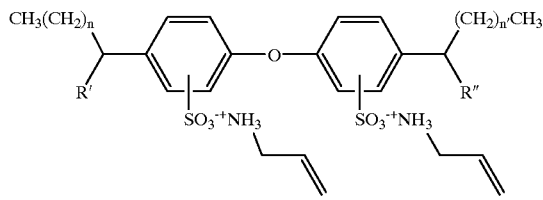

wherein n and n' are independently 4–18; and wherein R' and R" are independently hydrogen, methyl, ethyl or propyl.

The present invention may utilize secondary polymerizable surfactants of the formula:

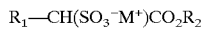

wherein $R_1$ and $R_2$ are independently saturated or unsaturated hydrocarbon groups having from about 1–24 carbon atoms; and wherein $M^+$ is a conjugate acid of the substantially saturated nitrogenous base. In a preferred embodiment, $R_1$ is a saturated or unsaturated hydrocarbon group having from about 6–24 carbon atoms, $R_2$ is methyl, ethyl, or propyl, or a mixture thereof, and $M^+$ is a conjugate acid of the snitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

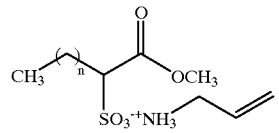

wherein n=3–18.

The present invention further utilizes surface active agents of the formula:

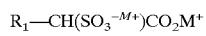

wherein $R_1$ is a saturated or unsaturated hydrocarbon group having from about 3–24 carbon atoms; and wherein $M^+$ is a conjugate acid of the nitrogenous base. In a preferred embodiment, $R_1$ is a saturated or unsaturated hydrocarbon group having from about 6–24 carbon atoms, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

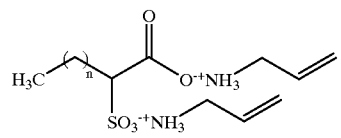

wherein n=3–18.

The present invention further utilizes surface active agents of the formula:

wherein $R_1$ and $R_2$ are independently saturated or unsaturated hydrocarbon groups having from about 1–24 carbon atoms; wherein R' is methyl or hydrogen; wherein n is an integer of from 1–100; and wherein $M^+$ is a conjugate acid of the nitrogenous base. In a preferred embodiment, $R_1$ is a saturated or unsaturated hydrocarbon group having from about 4–24 carbon atoms, R' is methyl or hydrogen, $R_2$ is methyl, ethyl, or propyl, and mixtures thereof, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, and n=1–100. In another preferred embodiment, the surface active agent is of the formula:

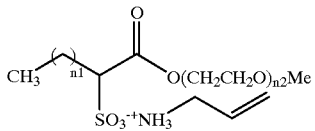

wherein n1=2–18; and wherein n2=1–20.

The present invention further utilizes surface active agents of the formula:

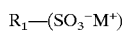

wherein $R_1$ is a saturated or unsaturated hydrocarbon group having from about 6–24 carbon atoms and wherein $M^++$ is a conjugate acid of the nitrogenous base. In a preferred embodiment, $R_1$ is a saturated or unsaturated hydrocarbon group having from about 6–24 carbon atoms, and $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

wherein n=5–17.

The present invention further utilizes surface active agents of the formula:

wherein $R_1$ and $R_2$ are independently saturated or unsaturated hydrocarbon groups having from about 1–24 carbon atoms; wherein n is zero or an integer of from 1–10; and wherein $M^+$ is a conjugate acid of the nitrogenous base. In a preferred embodiment, $R_1$ and $R_2$ are independently saturated or unsaturated hydrocarbon groups having from about 1–24 carbon atoms, n=1–6, and $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

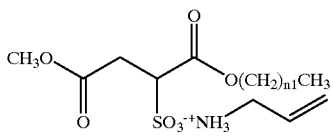

wherein n1 is zero or an integer of from 1–17

The present invention further utilizes surface active agents of the formula:

wherein $R_1$ is a saturated or unsaturated hydrocarbon group having from about 1–24 carbon atoms; wherein n=1–10; and wherein $M^+$ is a conjugate acid of the nitrogenous base. In a preferred embodiment, $R_1$ is a saturated or unsaturated hydrocarbon group having from about 6–24 carbon atoms, n=1–5, and $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, or a mixture thereof. In another preferred embodiment, the surface active agent is of the formula:

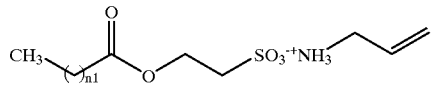

wherein n1=2–18.

The present invention further utilizes surface active agents of the formula:

wherein $R_1$ is a saturated or unsaturated hydrocarbon group having from about 1–24 carbon atoms; wherein Ar is a phenyl, polyphenyl, napthyl, polynapthyl, styryl, or polystyryl group, and mixtures thereof; wherein R' is methyl or hydrogen; wherein $M^+$ is a conjugate acid of the nitrogenous base; wherein n=1–5; wherein the total number of carbon atoms represented by $(R_1)_n$ is at least 5; and wherein m is zero or an integer of from 1–100. In a preferred embodiment, $R_1$ is a saturated or unsaturated hydrocarbon group having from about 6–24 carbon atoms, Ar is phenyl; $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, n=1, and m is zero or an integer of from 1–100. In another preferred embodiment, the surface active agent is of the formula:

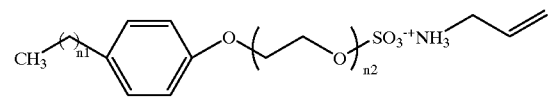

wherein n1=5–18; and wherein n2=0–20.

The present invention further utilizes surface active agents of the formula:

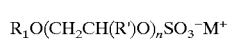

wherein $R_1$ is a saturated or unsaturated hydrocarbon group having from about 1–24 carbon atoms; wherein R' is methyl or hydrogen; wherein n=0–100; and wherein $M^+$ is a conjugate acid of the nitrogenous base. In a preferred embodiment, $R_1$ is a saturated or unsaturated hydrocarbon group having from about 6–24 carbon atoms, R' is methyl or hydrogen, n=0–100, and $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

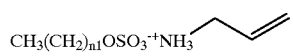

wherein n1=5–18. In another preferred embodiment, the surface active agent is of the formula:

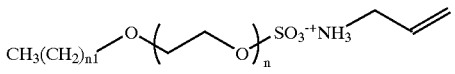

wherein n1=5–18; and wherein n=1–20.

The present invention further utilizes surface active agents of the formula:

$R_1CO_2^-M^+$ wherein $R_1$ is a saturated or unsaturated hydrocarbon group having from about 4–24 carbon atoms; and wherein $M^+$ is a conjugate acid of the nitrogenous base. In a preferred embodiment, $R_1$ is a saturated or unsaturated hydrocarbon group having from about 6–24 carbon atoms, and $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

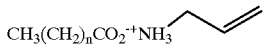

wherein n=5–18.

The present invention further utilizes surface active agents of the formula:

$R_1CON(R')(CH_2)_nCO_2^-M^+$ wherein $R_1$ is a saturated or unsaturated hydrocarbon group having from about 1–24 carbon atoms; wherein R' is methyl, ethyl, propyl or hydrogen; wherein $M^+$ is a conjugate acid of the nitrogenous base; and wherein n=1–10. In a preferred embodiment, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, R' is methyl, ethyl, propyl or hydrogen, and n=2–5. In another preferred embodiment, the surface active agent is of the formula:

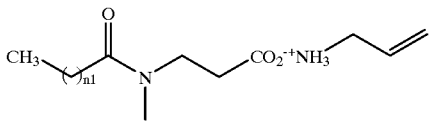

wherein n1=2–18.

The present invention farther utilizes surface active agents of the formula:

$R_1CON(R')(CH_2)_nSO_3M^+$ wherein $R_1$ is a saturated or unsaturated hydrocarbon group having from about 1–24 carbon atoms; wherein R' is methyl, ethyl, propyl or hydrogen; wherein $M^+$ is a conjugate acid of the nitrogenous base; and wherein n=1–10. In a preferred embodiment, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, R' is methyl, ethyl, propyl or hydrogen, and n=2–5. In another preferred embodiment, the surface active agent is of the formula:

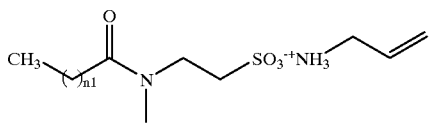

wherein n1=2–18.

The present invention further utilizes surface active agents of the formula:

$R_1O(CH_2CH(R')O)_nCOCH_2SO_3^-M^+$ wherein $R_1$ is a saturated or unsaturated hydrocarbon group having from about 1–24 carbon atoms; wherein R' is methyl or hydrogen; wherein n=0–100; wherein $M^+$ is a conjugate acid of the nitrogenous base. In a preferred embodiment, $R_1$ is a saturated or unsaturated hydrocarbon group having from about 6–24 carbon atoms; R' is methyl or hydrogen, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof; and n=0–100. In another preferred embodiment, the surface active agent is of the formula:

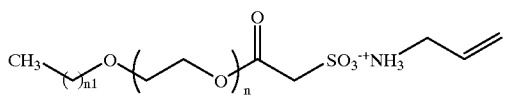

wherein n1=5–17; and wherein n=0–20.

The present invention further utilizes surface active agents of the formula:

$R_1O(PO_3)^{x-}M^+_y$ wherein $R_1$ is a saturated or unsaturated hydrocarbon group having from about 1–24 carbon atoms, phenyl, polyphenyl, napthyl, polynapthyl, styryl, or polystyryl group, an alkyl/alkoxylate substituted phenyl, an alkyl/alkoxylate substituted or poly-substituted polyphenyl, an alkyl/alkoxylate substituted or poly-substituted napthyl, an alkyl/alkoxylate substituted or poly-substituted polynapthyl, an alkyl/alkoxylate substituted or poly-substituted styryl, or an alkyl/alkoxylate substituted or poly-substituted polystyryl group, and mixtures thereof; wherein $M^+$ is a conjugate acid of the nitrogenous base; wherein x=1 or 2; and wherein y=1 or 2.

The present invention further utilizes surface active agents of the formula:

$[R_1O(CH_2CH(R')O)_m]_nP(O)_p^{x-}M^+_y$ wherein $R_1$ is a saturated or unsaturated hydrocarbon group having from about 1–24 carbon atoms; wherein R' is methyl or hydrogen; wherein $M^+$ is a conjugate acid of the nitrogenous base, the nitrogenous base selected from the group consisting of allyl amine, diallyl amine, triallyl amine, methallyl amine, N-methyl N-allyl amine, or 2-dimethylamino)ethyl acrylate, and mixtures thereof; m=0–100; wherein n=1 or 2; wherein p=2 or 3; wherein x=1 or 2; and wherein y=1 or 2.

The present invention further utilizes surface active agents of the formula:

wherein $R_1$ is a saturated or unsaturated hydrocarbon group having from about 1–24 carbon atoms; wherein Ar is phenyl; wherein R' is methyl or hydrogen; wherein $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof; wherein n=1–4; wherein m=0–100; wherein q=1 or 2; wherein p=2 or 3; wherein x=1 or 2; and wherein y=1 or 2.

Although less preferred, the present invention may utilizes polymerizable surface active agents which are quaternary ammonium salts of the general formula:

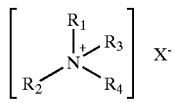

wherein $R_1$, $R_2$, $R_3$, and $R_4$ are independently, substituted or unsubstituted hydrocarbyl groups of from about 1 to about 30 carbon atoms, or hydrocarbyl groups having from about 1 to about 30 carbon atoms and containing one or more aromatic, ether, ester, amido, or amino moieties present as substituents or as linkages in the radical chain, wherein at least one of the $R_1$–$R_4$ groups contains at least one or more ethenylene groups; and wherein $X^-$ is an anion group selected from the group consisting of sulfonate, sulfate, sulfinate, sulfenate, phosphate, carboxylate, nitrate, and acetate. Additionally, useful polymerizable surface active agents include those of the above general formula in the form of ring structures formed by covalently linking two of the $R_1$–$R_4$ groups. Examples include unsaturated imidazolines, imidazoliniums, and pyridiniums, and the like. These quaternary ammonium salts may be prepared by a variety of methods known to the art, for example, halide exchange, wherein a halide based quaternary ammonium compound is ion exchanged with $X^-$, where $X^-$ is defined above.

The present invention encompasses amine oxide-derived polymerizable surface active agents, formed as shown in Scheme IX, wherein $R_1$, $R_2$, $R_3$ are independently, substituted or unsubstituted hydrocarbyl groups of from about 1 to about 30 carbon atoms, or hydrocarbyl groups having from about 1 to about 30 carbon atoms and containing one or more aromatic, ether, ester, amido, or amino moieties present as substituents or as linkages in the radical chain, wherein at least one of the $R_1$–$R_3$ groups contains at least one or more ethenylene groups; and wherein $X^-$ is an anion group selected from the group consisting of sulfonate, sulfate, sulfinate, sulfenate, phosphate, carboxylate, nitrate, and acetate. Additionally, useful polymerizable surface active agents include those of the above general formula in the form of ring structures formed by covalently linking two of the $R_1$–$R_4$ groups. Examples include unsaturated imidazolines, imidazoliniums, and pyridiniums, and the like.

Scheme IX
Amine Oxide-Derived Polymerizable Surface Active Agents

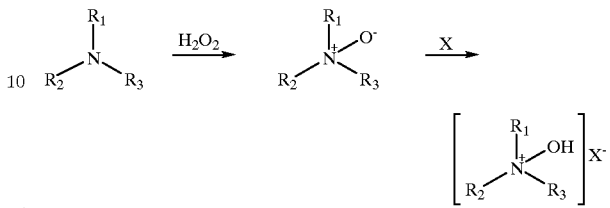

The present invention further encompasses quaternary halide-derived polymerizable surface active agents, formed as shown in Scheme X, wherein $R_1$, $R_2$, $R_3$ are independently, substituted or unsubstituted hydrocarbyl groups of from about 1 to about 30 carbon atoms, or hydrocarbyl groups having from about 1 to about 30 carbon atoms and containing one or more aromatic, ether, ester, amido, or amino moieties present as substituents or as linkages in the radical chain, wherein at least one of the $R_1$–$R_3$ groups contains at least one or more ethenylene groups; and wherein $X^-$ is an anion group selected from the group consisting of sulfonate, sulfate, sulfinate, sulfenate, phosphate, carboxylate, nitrate, and acetate. Additionally, useful polymerizable surface active agents include those of the above general formula in the form of ring structures formed by covalently linking two of the $R_1$–$R_4$ groups. Examples include unsaturated imidazolines, imidazoliniums, and pyridiniums, and the like.

The present invention further encompasses polymerizable onium compounds, particularly ammonium salts, sulfonium salts, sulfoxonium salts, oxonium salts, nitronium salts, and phosphonium salts of various anions, including for example, anions group selected from the group consisting of sulfonate, sulfate, sulfinate, sulfenate, phosphate, carboxylate, nitrate, acetate and various halides; wherein the onium compound contains at least one ethenylene functionality.

Auxiliary Polymerizable Surface Active Agents

The present invention encompasses the use of auxiliary polymerizable surface active agents, i.e. polymerizable surface active agent known to those skilled in the art, in combination with the polymerizable surface active agents, homopolymeric surface active agents, and supplemental surface active agents described herein. Examples of auxiliary polymerizable surface active agents useful in the present invention are shown below in Table I.

TABLE I

Auxillary Polymerizable Surface Active Agents

Diallyl Amine Pluronics -

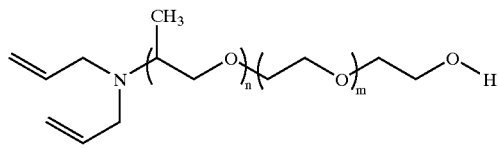

Linoleic Alcohol
ICI

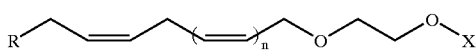

Allyl Alkyl Phenol
DKS

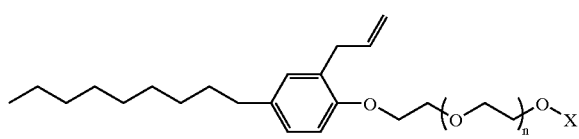

Acrylate Derivatives -

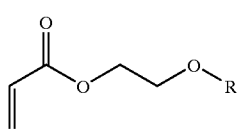

Allyl Alcohol Alkenyl
Anhydride Derivatives -
(Japan

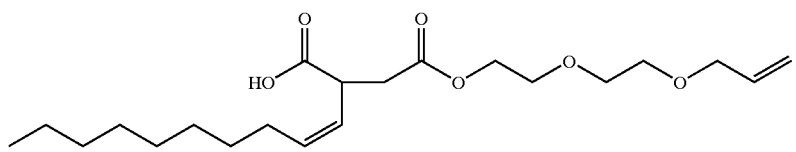

Polystep RA Series
Derivatives) - Stepan

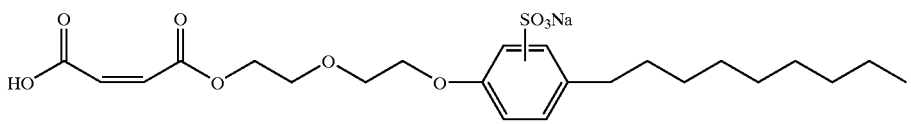

Maleic Derivatives -
Poulen

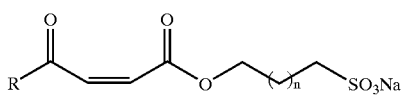

Trem LF-40
Sulfosuccinate
Henke

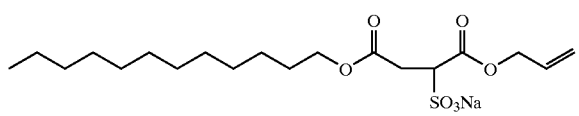

Additional auxiliary polymerizable surfactants useful herein, for example, are generally disclosed in *Polymerizable Surfactants* Guyot, A *Current Opinions in Colloid and Surface Science,* 1996, pg. 580–585; Reactive Surfactants in Emulsion Polymerization Guyot, A.; et. al; Advances in Polymer Science, Vol. 11, Springer-Verlag, Berlin, 1994, pg.43–65; and Polymerizable Surfactant, Holmberg, K., Progress in Organic Coatings, 20 (1992) 325–337 (all incorporated herein in their entirety).

Supplemental Surface Active Agents

Supplemental or primary surfactant components are optional in the inventive antimicrobial materials and prepolymerization mixtures. In certain situations, this surfactant component is necessary to maintain the stability of the latex composition. However, due to their migrating nature, conventional, non-polymerizable surface active agents are not favored in the invention. However, if so desired or required for stability, the polymerizable surface active agents of the present invention may be used in the polymerization in combination with appropriate amounts of a conventional polymerization surfactants, i.e. supplemental surface active agents, that are not polymerizable. Without being bound by any particular theory, these supplemental surface active agents may allow for the varying of particle size of the resulting discrete, solid, polymeric particles. The supplemental surface active agents are generally anionic, nonionic, cationic or amphoteric surfactants or mixtures thereof, and are typically used as in a concentration of about 0.01 to about 20.0 percent by weight, based on the total weight of surface active agents (i.e. both polymerizable and non-polymerizable). Somewhat more preferably, the supplemental surface active agents are used in a concentration of about 0.01 to about 5.0 percent by weight, based on the total weight of surface active agents (i.e. both polymerizable and non-polymerizable).

Where necessary to the preparation of the inventive materials, the weight ratio of the primary surfactant component to the surface active agent unit is from about 1:1 to 1:6. More preferred weight ratios of the primary surfactant component to the surface active agent unit are from about 1:2 to 1:4. A particularly preferred weight ratio of the primary surfactant component to the surface active agent unit is about 1:3.

Suitable supplemental nonionic surface active agents are generally disclosed in U.S. Pat. No. 3,929,678, Laughlin et al., issued Dec. 30, 1975, at column, 13 line 14 through column 16, line 6, incorporated herein by reference. Generally, the supplemental nonionic surface active agent is selected from the group comprising polyoxyethylenated alkylphenols, polyoxyethyleneated straight chain alcohols, polyoxyethyleneated branched chain alcohols, polyoxyethyleneated polyoxypropylene glycols, polyoxyethyleneated mercaptans, fatty acid esters, glyceryl fatty acid esters, polyglyceryl fatty acid esters, propylene glycol esters, sorbitol esters, polyoxyethyleneated sorbitol esters, polyoxyethylene glycol esters, polyoxyethyleneated fatty acid esters, primary alkanolamides, ethoxylated primary alkanolamides, secondary alkanolamides, ethoxylated secondary alkanolamides, tertiary acetylenic glycols, polyoxyethyleneated silicones, N-alkylpyrrolidones, alkylpolyglycosides, alkylpolylsaccharides, EO-PO block polymers, polyhydroxy fatty acid amides, amine oxides and mixtures thereof. Further, exemplary, non-limiting classes of useful supplemental nonionic surface active agents are listed below:

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to 12 carbon atoms in either a straight or branched chain configuration with the alkylene oxide. In a preferred embodiment, the ethylene oxide is present in an amount equal to from about 1 to about 25 moles of ethylene oxide per mole of alkyl phenol. Commercially available nonionic surfactants of this type include Igepal® CO-630, marketed by Stepan Company, Canada; and Triton® X-45, X-114, X-100 and X-102, all marketed by the Union Carbide Company.

2. The condensation products of aliphatic alcohols with from about 1 to about 25 moles of ethylene oxide. The alkyl chain of the aliphatic alcohol can either be straight or branched, primary or secondary, and generally contain from about 8 to about 22 carbon atoms. Particularly preferred are the condensation products of alcohols having an alkyl group containing from about 6 to about 11 carbon atoms with from about 2 to about 10 moles of ethylene oxide per mole of alcohol. Examples of commercially available nonionic surfactants of this type include Tergitol® 15-S-9 (the condensation products of $C_{11}$–$C_{15}$ linear alcohol with 9 moles of ethylene oxide), Tergitol® 24-L-6 NMW (the condensation products of $C_{12}$–$C_{14}$ primary alcohol with 6 moles of ethylene-oxide with a narrow molecular weight distribution), both marketed by Union Carbide Corporation; Neodol® 91-8 (the condensation product of $C_9$–$C_{11}$ linear alcohol with 8 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 91-6 (the condensation product of $C_9$–$C_{11}$ linear alcohol with 6 moles of ethylene oxide), marketed by Shell Chemical Company, and Kyro® EOB (the condensation product of $C_{13}$–$C_{15}$ linear alcohol with 9 moles of ethylene oxide), marketed by the Procter and Gamble Company.

3. The condensation products of ethylene oxide with a hydrophobic base formed by the condensation of propylene oxide with propylene glycol. The hydrophobic portion of these compounds preferably has a molecular weight of from about 1500 to about 1880 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic® surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic® compounds, marketed by BASF.

5. Semi-polar nonionic surfactants are a special category of supplemental nonionic surface active agents which include water-soluble amine oxides containing on alkyl moiety of from about 10 to about 18 carbon atoms and 2 moieties selected from the group comprising alkyl groups and hydroxyalkyl groups containing from about 1 to about 3 carbon atoms; and water-soluble sulfoxides containing alkyl moieties of from about 10 to about 18 carbon atoms and a moiety selected from the group comprising alkyl groups and hydroxyalkyl groups of from about 1 to about 3 carbon atoms.

6. Alkylpolysaccharides disclosed in U.S. Pat. No. 4,565,647, Lenado, issued Jan. 21, 1986, incorporated herein by reference, having a hydrophobic group containing from about 6 to about 30 carbon atoms, preferably from about 10 to about 16 carbon atoms and a polysaccharide, e.g., a polyglucoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally, the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

7. An ethyl ester ethoxylate and/or alkoxylate such as those described in U.S. Pat. No. 5,220,046, incorporated herein by reference. These material may be prepared according to the procedure set forth in Japanese Kokai patent application No. HEI 5 [1993]-222396. For example, they may be prepared by a one-step condensation reaction between an alkyl ester and an alkylene oxide in the present of a catalytic amount of magnesium together with another ion selected from the group of $Al^{+3}$, $Ga^{+3}$, $In^{+3}$, $Co^{+3}$, $Sc^{+3}$, $La^{+3}$ and $Mn^{+3}$.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched, containing from about 8 to about 18, preferably from about 12 to about 14 carbon atoms; n is 2 or 3, preferably 2; t is from about 0 to about 10, preferably 0; and x is from about 1.3 to about 10, preferably from about 1.3 to 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glucosyl units can then be attached between their 1-position and the preceding glycosyl units 2-, 3-, 4-, and/or 6-position, preferably predominately the 2-position.

Examples of suitable supplemental amphoteric surface active agents are selected from the group comprising alkyl glycinates, propionates, imidazolines, amphoalkylsulfonates sold as "Miranol"® by Rhone Poulenc, N-alkylaminopropionic acids, N-alkyliminodipropionic acids, imidazoline carboxylates, N-alkylbetaines, amido propyl betaines, sarcosinates, cocoamphocarboxyglycinates, amine oxides, sulfobetaines, sultaines and mixtures thereof. Additional suitable amphoteric surfactants include cocoamphoglycinate, cocoamphocarboxyglycinate, lauramphocarboxyglycinate, cocoamphopropionate, lauramphopropionate, stearamphoglycinate, cocoamphocarboxy-propionate, tallowamphopropionate, tallowamphoglycinate, oleoamphoglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocamphopropylsulfonate, stearamphopropyl-sulfonate, oleoamphopropylsulfonate and the like.

Examples of supplemental amine oxide surface active agents which are generally suitable for use in the present invention are alkylamine and amidoamine oxides. Examples of supplemental betaine and sultaine surface active agents which are suitable for use in the present invention are alkyl betaines and sultaines sold as "Miratine"® by Rhone Poulenc, "Lonzaine"® by Lonza, Inc., Fairlawn, N.J. Examples of supplemental betaines and sultaines are cocobetaine, cocoamidoethyl betaine, cocoamidopropyl betaine, lauryl betaine, lauramidopropyl betaine, palmamidopropyl betaine, stearamidopropyl betaine, stearyl betaine, coco-sultaine, lauryl sultaine, tallowamidopropyl hydroxysultaine and the like.

Examples of supplemental cationic surface active agents useful in the present invention are fatty amine salts, fatty diamine salts, polyamine salts, quaternary ammonium compounds, polyoxyethyleneated fatty amines, quaternized polyoxyethyleneated fatty amines, amine oxides and mixtures thereof.

Examples of suitable supplemental cationic surface active agents are disclosed in the following documents, all incorporated by reference herein: M.C. Publishing Co., *McCutcheon's Detergents & Emulsifiers*, (North American Ed., 1993); Schwartz et al., *Surface Active Agents, Their Chemistry and Technology*, New York; Interscience Publisher, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Examples of supplemental cationic surface active agents in the form of quaternary ammonium salts include dialkyldiethyl ammonium chlorides and trialkyl methyl ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from about 16 to about 18 carbon atoms). Examples of supplemental quaternary ammonium salts useful herein include ditallowdimethyl ammonium chloride, ditallowdimethyl ammonium methyl sulfate, dihexadecyl dimethyl ammonium chloride, di-(hydrogenated tallow) dimethyl ammonium chloride, dioctadecyl dimethyl ammonium chloride, dieicosyl dimethyl ammonium chloride, didocosyl dimethyl ammonium chloride, di-(hydrogenated tallow) dimethyl ammonium acetate, dihexadecyl dimethyl ammonium chloride, dihexadecyl dimethyol ammonium acetate, ditallow dipropyl ammonium phosphate, ditallow dimethyl ammonium nitrate, di-(coconutalkyl) dimethyl ammonium chloride, and stearyl dimethyl benzyl ammonium chloride.

Salts of primary, secondary and tertiary fatty amines are also suitable supplemental cationic surface active agents. The alkyl groups of such supplemental amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable supplemental amine salts include the halogen, acetate, phosphate, nitrate, citrate, lactate and alkyl sulfate salts. Such supplemental salts include stearylamine hydrogen chloride, soyamine chloride, stearylamine formate, N-tallowpropane diamine dichloride and stearamidopropyl dimethylamine citrate. Supplemental cationic amine surfactants included among those useful in the present invention are also disclosed in U.S. Pat. No. 4,275,055, Nachtigal, et al., issued Jun. 23, 1981, incorporated herein by reference.

Supplemental cationic surface active agents which are especially useful are quaternary ammonium or amino compounds having at least one N-radical containing one or more nonionic hydrophilic moieties selected from the group comprising alkoxy, polyoxyalkylene, alkylamido, hydroxyalkyl, and alkylester moieties, and combinations thereof. The compounds contain at least one hydrophilic moiety within 4, preferably within 3, carbon atoms (inclusive) of the quaternary nitrogen or cationic amino nitrogen. Additionally, carbon atoms that are part of a hydrophilic moiety, e.g., carbon atoms in a hydrophilic polyoxyalkylene (e.g., —$CH_2$—$CH_2$—O—), that are adjacent to other hydrophilic moieties are not counted when determining the number of hydrophilic moieties within 4, or preferably 3, carbon atoms of the cationic nitrogen. In general, the alkyl portion of any hydrophilic moiety is preferably a $C_1$-$C_3$ alkyl. Suitable hydrophile-containing radicals include, for example, ethoxy, propoxy, polyoxyethylene, polyoxypropylene, ethylamido, propylamido, hydroxymethyl, hydroxyethyl, hydroxypropyl, methyl ester, ethyl ester, propyl ester, or mixtures thereof, as nonionic hydrophile moieties.

Among the supplemental cationic surface active agents useful herein are those of the general formula:

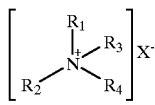

wherein $R_1$, $R_2$, $R_3$, and $R_4$ comprise, independently, substituted or unsubstituted substantially saturated hydrocarbyl chains of from about 1 to about 30 carbon atoms, or a hydrocarbyl having from about 1 to about 30 carbon atoms and containing one or more aromatic, ether, ester, amido, or amino moieties present as substituents or as linkages in the radical chain, wherein at least on of the $R_1$–$R_4$ groups contains one or more hydrophilic moieties selected from the group comprising alkoxy (preferably $C_1$–$C_3$ alkoxy), polyoxyalkylene (preferably $C_1$–$C_3$ polyoxyalkylene), alkylamido, hydroxyalkyl, alkylester and combination thereof. Preferably, the cationic conditioning surfactant contains from about 2 to about 10 nonionic hydrophile moieties located within the about stated ranges. For purposes herein, each hydrophilic amido, alkoxy, hydroxyalkyl, alkylester, alkylamido or other unit is considered to be a distinct nonionic hydrophile moiety. $X^-$ is a substantially saturated soluble salt forming anion preferably selected from the group comprising halogens (especially chlorine), acetate, phosphate, nitrate, sulfonate, and alkyl sulfate radicals.

Preferred supplemental cationic surface active agents include polyoxyethylene (2) stearyl methyl ammonium chloride, methyl bis-(hydrogenated tallowamidoethyl) 2-hydroxyethyl ammonium methyl sulfate, polyoxypropylene (9) diethyl methyl ammonium chloride, tripolyoxyethylene (total PEG-10) stearyl ammonium phosphate, bis-(N-hydroxyethyl-2-oleyl imidazolinium chloride) polyethylene glycol (1), and isododecylbenzyl triethanolammonium chloride.

Other supplemental ammonium quaternary and amino surface active agents include those of the above general formula in the form of ring structures formed by covalently linking two of the radicals. Examples include imidazolines, imidazoliniums, and pyridiniums, etc., wherein said compound has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxoctadecyl)oxy]ethyl]amino]ethyl] pyridinium chloride.

Salts of primary, secondary and tertiary fatty amines are also preferred supplemental cationic surfactant materials. The alkyl groups of such amines preferably have from about 1 to about 30 carbon atoms and must contain at least one, preferably about 2 to about 10, nonionic hydrophilic moieties selected from the group comprising alkoxy, polyoxyalkylene, alkylamido, hydroxyalkyl, and alkylester groups, and mixtures thereof.

The supplemental anionic surface active agents suitable for use in the present invention are generally the sodium, potassium, calcium, ammonium or alkanolamine salts of any substantially saturated sulfonic acid, carboxylic acid, or phosphoric acid, or a mixture thereof. More specifically, supplemental anionic surface active agents suitable for use in the present invention are generally the sodium, potassium, calcium, ammonium or alkanolamine salts of saturated sulfonic acids, sulfinic acids, sulfenic acids, sulfonic acid esters, carboxylic acids, phosphonic acids, phosphinic, phosphenic acids, polysulfonic acids, sulfonic acids of oils, paraffin sulfonic acids, lignin sulfonic acids, petroleum sulfonic acids, tall oil acids, olefin sulfonic acids, hydroxyolefin sulfonic acids, polyolefin sulfonic acids, polyhydroxy polyolefin sulfonic acids, carboxylic acids, perfluorinated carboxylic acids, carboxylic acid sulfonates, alkoxylated carboxylic acid sulfonic acids, polycarboxylic acids, polycarboxylic acid polysulfonic acids, alkoxylated polycarboxylic acid polysulfonic acids, phosphoric acids, alkoxylated phosphoric acids, polyphosphoric acids, and alkoxylated polyphosphoric acids, fluorinated phosphoric acids, phosphoric acid esters of oils, phosphinic acids, alkylphosphinic acids, aminophosphinic acids, polyphosphinic acids, vinyl phosphinic acids, phosphoric acids, polyphosphonic acids, phosphoric acid alkyl esters, α-phosphono fatty acids, oragnoamine polymethylphosphonic acids, organoamino dialkylene phosphoric acids, alkanolamine phosphoric acids, trialkyledine phosphoric acids, acylamidomethane phosphoric acids, alkyliminodimethylene diphosphonic acids, polyethylene-bis(nitrilodimethylene)tetraphosphonic acids, alkyl bis (phosphonoalkylidene) amine oxide acids, esters of substituted aminomethylphosphonic acids, phosphonamidic acids, acylated amino acids (e.g., amino acids reacted with alkyl acyl chlorides, alkyl esters or carboxylic acids to produce N-acylamino acids), N-alkyl acylamino acids, and acylated protein hydrolysates, and mixtures thereof.

Other supplemental anionic surface active agents suitable for use in the present invention are the sodium, potassium, calcium, ammonium or alkanolamine salts of saturated linear or branched alkylbenzene sulfonic acids, alkyl sulfuric acid esters, alkoxylated alkyl sulfuric acid esters, α-sulfonated alkyl ester acids, α-sulfonated ester diacids, alkoxylated α-sulfonated alkyl ester acids, α-sulfonated dialkyl diester acids, di-α-sulfonated dialkyl diester acids, α-sulfonated alkyl acetate acids, primary and secondary alkyl sulfonic acids, perfluorinated alkyl sulfonic acids, sulfosuccinic mono- and diester acids, polysulfosuccinic polyester acids, sulfoitaconic diester acids, sulfosuccinic acids, sulfosuccinic amide acids, sulfosuccinic imide acids, phthalic acids, sulfophthalic acids, sulfoisophthalic acids, phthalamic acids, sulfophthalic acids, alkyl ketone sulfonic acids, hydroxyalkane-1-sulfonic acids, lactone sulfonic acids, sulfonic acid amides, sulfonic acid diamides, alkyl phenol sulfuric acid esters, alkoxylated alkyl phenol sulfuric acid esters, alkylated cycloalkyl sulfuric acid esters, alkoxylated alkylated cycloalkyl sulfuric acid esters, dendritic polysulfonic acids, dendritic polycarboxylic acids, dendritic polyphosphoric acids, sarcosinic acids, isethionic acids, and tauric acids, and mixtures thereof.

Additionally in accordance with the present invention, supplemental anionic surface active agents suitable for use in the present invention are generally the sodium, potassium, calcium, ammonium or alkanolamine salts of saturated fluorinated carboxylic acids, fluorinated sulfonic acids, fluorinated sulfate acids, fluorinated phosphoric and phosphinic acids, and mixtures thereof.

In a preferred embodiment of the present invention, the polymerization process is conducted in the absence of any non-polymerizable, supplemental surfactant, as the polymerizable surface active agents of the present invention display excellent capacity for producing emulsion stability characteristics in an emulsion polymerization.

In another embodiment of the present invention, the polymerizable surface active agents of the present invention may be used as co-monomers with the ethylenically unsaturated monomer(s) to modify the physical properties of the resulting polymer. In this embodiment, supplemental surface active agents also may be used as additives to the polymerization, e.g., in amounts of from about 3 to 6 weight percent, based on the total weight of monomer. Although somewhat less preferred, in a further embodiment of the present invention, any conventional organic solvent, which may be a solvent for both the monomer(s) and/or polymer, or just the monomer(s) may be used.

Initiators and Additives

Organic or inorganic initiators may be used to initiate the polymerization reaction. A sufficient quantity of a polymerization initiator (such as a conventional free radical initiator) is typically introduced into the polymerization medium to cause polymerization of the monomer(s) at the particular temperatures employed. Initiators used in polymerization processes may be of the type which produce free radicals and conveniently are peroxygen compounds, for example: inorganic peroxides such as hydrogen peroxide and inorganic persulfate compounds such as ammonium persulfate, sodium persulfate and potassium persulfate; organic hydroperoxides such as cumene hydroperoxide and tertiary butyl hydroperoxide; organic peroxides such as benzoyl peroxide, acetyl peroxide, lauroyl peroxide, peroxydicarbonate esters such as diisopropyl peroxydicarbonate, peracetic acid and perbenzoic acid, sometimes activated by water-soluble reducing agents such as ferrous compounds, sodium bisulfite or hydroxylamine hydrochloride, and other free radical producing materials such as 2,2'-azobisisobutyronitrile.

A further additive which may be added to the mixture contents is a conventional chain transfer agent, such as an alkyl polyhalide or mercaptan. Examples of suitable chain transfer agents include bromoform, carbon tetrachloride, carbontetrabromide, bromoethane, $C_1$–$C_{12}$ alkyl mercaptans, e.g., dodecylmercaptan, thiophenol, hydroxyalkyl mercaptans, e.g., mercaptoethanol and diacrylates to increase molecular weight.

Compositions

Antimicrobial CASE Materials

General Descriptions and Ingredients

The antimicrobial compositions of the invention may take the form of a coating, adhesive, sealant or elastomer. Such compositions are referred to as antimicrobial CASE materials. These compositions and materials are described in more detail below.

Coatings and Paints

Paints are typically liquids which are useful for application to a substrate, such as wood, metal, glass, ceramics, fiberglass, composite materials, cardboard, corrugated board, paper, textiles, non-woven materials, plastic, foam, tape or a combination thereof, in a thin layer. Paints are typically used to protect the surface of the substrate from elemental damage and/or physical damage. Paints are also commonly used for decoration and aesthetic purposes. Paints find very broad commercial use and also find a variety of uses in the home. Paints, their formulations, ingredients, additives and processing conditions are generally described in Kirk-Othmer-Paint; pg. 1049–1069, Vol. 17; 1996, by Arthur A. Leman, the disclosure of which is incorporated herein in its entirety.

Typically, paints are described as latex, alkyd, or oil-based paints. Additionally, a wide variety of paints are water-based. These designations identify the binder used in the manufacture of the paint and the solvent, if any, which is used. Typically classes of latex paints include gloss, semi-gloss, flat, and satin. These terms describe the shininess of the paint surface after the paint has dried on the substrate. Paints typically contain binders/resins, such as latex emulsions. A common latex emulsion employed in paints is based on acrylic and vinyl acetate Paints often include pigments (organic and inorganic), inorganic extenders, filler pigments, solvents, and additives, such as thickeners, protective colloids, biocides, driers, pigment dispersants, pigment extenders, adhesion promoters, surfactants, and defoamers. When paints are manufactured, surface active agents are used to stabilize the emulsion polymerization and also regulate the resulting polymer particle size.

The aforementioned monomers may be utilized to prepare latexes useful in coatings and paints of the instant invention. Typically the monomers are selected to give an acrylic latex emulsion, for durable exterior paint. These monomers are preferably methyl methacrylate, butyl acrylate, and 2-ethylhexyl acrylate, and mixtures thereof. Non-acrylic based monomers are typically used for interior paints, except in the cases of gloss and semi-gloss paints. Among other monomers, vinyl acetate, butyl acrylate and mixtures thereof, are commonly used in a variety of paint formulations.

Alkyd resins are produced by reaction of a polybasic acid, such as phthalic or maleic anhydride, with a polyhydric alcohol, such as glycerol, pentaerythitol, or glycol, in the presence of an oil or fatty acid." (See Kirk-Othmer-Paint; pg. 1049–1069; Vol. 17; 1996; Arthur A. Leman). "Alkyd resins are described as long-oil, medium-oil, and short-oil alkyds. Such description is based on the amount of oils and/or fatty acids in the resins. Long-oil alkyds generally have an oil content of 60% or more; short-oil alkyds, less than 45%; and medium-oil alkyds have an oil content in between the two. The short- and medium-oil alkyds are based on semidrying and nondrying oils, whereas long-oil alkyds are based on semidrying and drying oils.

Typical pigment extenders used in paints include, for example, titanium dioxide, calcium carbonate, talc, clay, silica, zinc oxide, feldspar, corrosion resistance extenders, mildew resistance extenders, and film-hardening extenders, and mixtures thereof. Solvents typically used in paints included, for example, mineral spirits, glycol ethers (e.g. ethylene glycol and propylene glycol) and the like. In addition to binders, solvents, pigments, and extenders, many paints contain additives. Additives include, for example, thickeners, pigment dispersants, surfactants, defoamers, biocides, mildewcides, preservatives, driers, defoamers, antiskinning agents and pH adjusting agents and mixtures thereof (e.g. acids and bases). Additional additives include hydroxyethylcellulose, hydrophobically modified alkali-soluble emulsions, and hydrophobically modified ethylene oxide urethanes.

Adhesives and Sealants

Sealants have been generally described in Kirk-Othmer-Sealants; pg. 650–666; Vol. 21; 1997, by Richard Palmer and Jerome Kloswski, the disclosure of which is incorporated herein in its entirety. "A sealant is a material that is installed into a gap or joint to prevent water, wind, dirt, or other contaminants from passing through the joint or gap. Sealants, which can also be defined by how they are tested, are rated by their ability to stretch, twist, bend, and be compressed while maintaining their bulk properties so they do not tear apart under stress. The adhesion required of a sealant is simply the strength to hold the sealant in position as it is stressed and strained. Adhesives are used to transfer loads and are typically designed with much higher tensile and shear strengths than sealants. The most important rating of an adhesive in many applications is the determination of how much load it can handle. Some sealants are used as adhesives and some adhesives as sealants and thus arises the occasional blurring of their roles. If the material's primary function is the exclusion of wind, water, dirt, etc., it is a sealant.

Sealants include high performance sealants, such as for example, silicones, urethanes, and polysulfides, medium performance sealants, such as for example, acrylic sealants, and low performance sealants, such as for example, butyls, putties, and caulks. "The measure of the stress of a sealant at a specific strain is referred to as the modulus of elasticity, sometimes called the secant modulus. This important sealant property describes the force exerted by a sealant as it is stressed. Because a primary function of sealants is to adhere to the substrates it is in contact with, the force generated by a joint opening or closing are transmitted by the sealant to the substrate-sealant bond line. A primary factor in sealant durability is its ability to resist decay from environmental elements. For most typical applications this includes extremes of high and low temperature, water, oxidation, and sunlight." Other factors include weatherability and adhesion life. One of the more destructive elements is exposure to sunlight; specifically, ultraviolet (UV) light. All sealants are affected by weathering but there is much difference in the effect of weathering on different sealants. A second key factor in determining the durability of a sealant is the ability of the sealant to adhere to the substrate through its lifetime. A sealant may have excellent resistance to uv effects, but if it has poor adhesion performance and fails adhesively, it is of little use.

Commercially available silicone sealants are typically one of three curing types: moisture-reactive (curing) sealants, moisture-releasing (latex) sealants, and addition-curing sealants. The formulation of moisture-curing silicones includes a silicone polymer, filler, a moisture-reactive cross linker, and sometimes a catalyst. A newer class of silicone sealants are known as the silicone latex sealants. These sealants are silicone-in-water emulsions that cure by evaporation of the emulsifying water. The silicone latex polymer is prepared by first emulsifying a low molecular weight silicone polymer in water and then polymerizing it to the desired molecular weight. Inherent to emulsion polymerization is the ability to produce high molecular weight polymers at a low emulsion viscosity. Next, a silicone cross-linker is added with a condensation catalyst. The cross-linker, the structure of which is similar to those described previously, must diffuse through the water phase and into the siloxane phase where it can react with the silicone polymer. Addition-curing silicones in general are two-part systems that cure by the platinum-catalyzed reaction of a silicon hydride with typically a vinyl group attached to silicon. The basis for urethane chemistry is the reaction of an isocyanate group with a component containing an active hydrogen. The first step in formulating a urethane sealant is to prepare what is commonly called the prepolymer, typically by reaction of a hydroxy-terminated polyether with a stoichiometric amount of diisocyanate. Polysulfide sealants were the first high performance synthetic elastomeric sealants produce in the United States. The basic polymers are mercaptan-terminated (HS-R-SH), with molecular weights ranging from 1000 to ca 8000.

There are two principal classes of acrylic sealants: latex acrylics and solvent-release acrylics. High molecular weight latex acrylic polymers are prepared by emulsion polymerization of alkyl esters of acrylic acid. Monomer, water, surfactants, and an initiator are mixed and polymerized until the acrylic monomer is depleted. Two types of monomers are used to vary polymer properties. High $T_g$ monomers such as methyl methacrylate and vinyl chloride improve durability and hydrophobicity, whereas polar-functional monomers such as hydroxyethyl acrylate are used to improve adhesion. The maximum levels of solids for the latex polymer is approximately 60%. In typical formulations, above this point the viscosity increases rapidly and the emulsion stability is poor. In relatively low solids (high water) content formulations, rather severe shrinkage occurs during cure. This can introduce stress and may be one of the reasons most latex acrylics are of lower performance and lower movement ability. The surfactants used are of special concern to sealant formulation because they can interfere with adhesion if improperly used. One approach to solve this problem is in corporate the surfactant into the polymer backbone during polymerization. This approach, which places the surfactant in an ideal location to stabilize the emulsion, does not allow the surfactant to migrate through the aqueous phase and interfere with adhesion because the surfactant is connected to the backbone (13). The emulsion polymers are compounded into sealants by adding fillers, plasticizers, freeze-thaw stabilizers, thickeners, and adhesions promoters. As is true of the silicone sealants, the acrylic sealants are easy to apply and clean with water.

Another class of acrylic sealants are the solvent-releasing acrylics. Acrylic monomers are polymerized in a solvent. The molecular weight of the polymer is lower than in the latex acrylics because of the inherently higher viscosity of the medium. However, the percentage of solids is approximately 80% vs the 60% common to latex acrylics. The natural adhesion of most of the solvent-releasing acrylics produces some of the best unprimed adhesion in the sealant industry. However, slow, continual cure generally produces large compression sets and limits their use to low movement application. Also, the relatively high amounts of solvent and traces of acrylic monomer in these functions limits their use to outdoor applications, usually in construction.

A typical one-part pigmented siliconized acrylic latex sealant will contain acrylic latex polymer (polymer and water), and optional ingredients selected from calcium carbonate, plasticizers, mineral spirits, propylene glycol, titanium dioxide, ammonium hydroxide, preservatives, surfactants, inorganic dispersants, organic dispersants, defoamers, associative thickener, and silane adhesion promoters, and mixtures thereof.

A typical one-part clear acrylic latex sealant formulation will contain acrylic latex polymer (polymer and water) and optional ingredients selected from plasticizers, fumed silica, surfactants, amino silanes, and ammonium hydroxides and mixtures thereof. Almost all sealants contain a mixture of a powdered filler incorporated into a viscous liquid, which results in a viscous sealant having a paste-like consistency.

Adhesives have been generally described in Kirk-Othmer-Adhesives; pg. 445–466; Vol. 1; 1991, by Aldophus Pocius, the disclosure of which is incorporated herein in its entirety. An adhesive is a material capable of holding together solid materials by means of surface attachment. Adhesion is the physical attraction of the surface of one material for the surface of another. An adherend is the solid material to which the adhesive adheres and the adhesive bond or adhesive joint is the assembly made by joining adherends together by means of an adhesive. Practical adhesion is the physical strength of an adhesive bond. It primarily depends on the forces of the adhesive and the adherend, as well as the engineering of the adhesive bond. The interphase is the volume of materials in which the properties of one substance gradually change into the properties of another. The interphase is useful for describing the properties of an adhesive bonds. The interface, contained within the interphase, is the plane of contact between the surface of one material and the surface of another. Except in certain special cases, the interface is imaginary. It is useful in describing surface energetics.

Adhesive properties are often tested using various peel tests. In the simplest peel test, the T-peel test, the adherends are identical in size, shape, and thickness. Adherends are attached at their ends to a tensile testing machine and then separated in a "T" fashion. The temperature of the test, was well as the rate of adherend separation, is specified. The force required to open the adhesive bond is measured and the results are reported in terms of newtons per meter (pounds per inch, ppi). There are many other peel test configurations, each dependent upon the adhesive application. Such tests are well described in the ASTM literature.

A structural adhesive is a resin system, usually a thermoset, that is used to bond high strength materials in such a way that the bonded joint is able to bear a load in excess of 6.9 MPa (1,000 psi) at room temperature. Structural adhesives are the strongest form of adhesive and are meant to hold loads permanently. They exist in a number of forms. The most common form is the two-part adhesive, widely available as a consumer product. The next most familiar is that which is obtained as a room temperature curing liquid. Less common are primer-liquid adhesive combinations which cure at room temperature.

A pressure-sensitive adhesive, a material which adheres with no more than applied finger pressure, is aggressively and permanently tacky. It requires no activation other than the finger pressure, exerts a strong holding force, and should be removable from a smooth surface without leaving a residue. Pressure-sensitive adhesives are most widely used in the form of adhesive tapes. These tapes are used for an extraordinary number of applications: masking, medical application, electrical insulation, assembly, packaging, and other application. The application governs the choice of tape backing and the adhesive formulation. A transparent backing having relatively weak adhesive is used for paper mending; a filament filled backing having an aggressive adhesive is used for packaging applications. Pressure-sensitive adhesives are also obtainable in aerosol form for use in various graphics.

The general formula for a pressure-sensitive adhesive includes elastomeric polymer, a tackifying resin, any necessary fillers, various antioxidants and stabilizers, if needed, and cross-linking agents. In formulating a pressure-sensitive adhesive, a balance of three physical properties needs to be taken into account: sheer strength, peel strength, and tack. The shear strength or shear holding power of the adhesive is typically measured by hanging a weight on the end of a piece of tape and measuring the time of failure. Tack is the technical term applied to quantify the sticky feel of the material. in general, the shear strength and the tack of a pressure-sensitive adhesive increase and then go through a maximum as a function of the amount of tackifying resin added. The peel strength usually increases with the amount of tackifying resin. The shear holding power often depends upon the mode of cross-linking. This, a balance of properties appropriate to the application is obtained by controlling the rubber-to-resin ratio as well we the level and type of cross-linking agent.

The most widely used emulsion-based adhesives is that based upon poly(vinyl acetate)-poly(vinyl alcohol) copolymers formed by free-radical polymerization in an emulsion system. Poly(vinyl alcohol) is typically formed by hydrolysis of the poly(vinyl acetate). The properties of the emulsion are derived from the polymer employed in the polymerization as well as from the system used to emulsify the polymer in water. The emulsion is stabilized by a combination of a surfactant plus a colloid protection system. The protective colloids are similar to those used in paint (qv) to stabilize latex. For poly(vinyl acetate), the protective colloids are isolated from natural gums and cellulosic resins (carboxymethylcellouse or hydroxyethylcellous). The hydrolyzed polymer may also be used. The physical properties of the poly(vinyl acetate) polymer can be modified by changing the co-monomer used in polymerization. Any material which is free-radically active and participates in a n emulsion polymerization can be employed. Plasticizers (qv), tackifiers, humectants, and other materials are often added to the adhesive to meet specifications for the intended application. Because the presence of foam in the bond line could decrease performance of the adhesion joint, agents that control the amount of air entrapped in an adhesive bond must be added. Biocides are also necessary: many of the materials that are used to stabilize poly(vinyl acetate) emulsions are natural products. Poly(vinyl acetate) adhesives known as "white glue" or "carpenter's glue" are available under a number of different trade names. Application are found mostly in the are of adhesion to paper and wood.

Elastomers

Elastomers have been generally described in Kirk-Othmer-Elastomers; pg. 905–1079; Vol. 8; 1993; and Kirk-Othmer-Elastomers; pg. 1–31; Vol. 9; 1994, by various authors, the disclosure of which is incorporated herein in its entirety. The term elastomer is the modern word to describe a material that exhibits rubbery properties, i.e., that can recover most of its original dimensions after extension of compression. Once key class of elastomers is rubber materials. "Rubber materials, e.g., natural, SBR, or polybutadiene, being unsaturated hydrocarbons, are subjected to sulfur vulcanization, and this process requires certain ingredients in the rubber compound, besides the sulfur, e.g., accelerator, zinc oxide, and stearic acid. Accelerators are catalysts that accelerate the cross-linking reaction so that reaction time drops from many hours to perhaps 20–30 min. at about 130° C. In addition to the ingredients that play a role in the actual vulcanization process, there are other components that make up a typical rubber compound.

Softeners and extenders, generally inexpensive petroleum oils, help in the mastication and mixing of the compound. Antioxidants are necessary because the unsaturated rubbers can degrade rapidly unless protected from atmospheric oxygen. They are generally organic compounds of the amine or phenol type. Reinforcing fillers, e.g. carbon black or silica, can help enormously in strengthening the rubber against rupture or abrasion. Nonreinforcing fillers, e.g., clay or chalk, are used only as extenders and stiffeners to reduce cost.

For Styrene-Butadiene Rubber (SBR), the polymerization is carried out in an emulsion system where a mixture of the two monomers is mixed with a soap [or other surface active agent] solution containing the necessary catalysts (initiators). The final product is an emulsion of the copolymer, i.e., a fluid latex.

Inventive Antimicrobial CASE Materials

The present invention embodies CASE materials which comprise polymer particles or a polymer latex (derived from the aforementioned polymers formed from the use of polymerizable surface active agents). These CASE materials may additionally contain standard ingredients, including those previously mentioned, as used by those of ordinary skill in the art to prepare such CASE materials. The CASE materials of the present invention may be formulated for the chosen end use. The CASE materials are prepared by conventional techniques which are known in the art. The CASE materials may be applied to various substrates by methods known in the art, such as for example, air-assisted spray, airless spray, brush, direct coat or transfer coat, roller, caulk-gun, and the like. Adhesives, sealants and elastomers may be applied by a wide variety of application devices typically used for such a purpose.

As mentioned, the CASE sealants and adhesives may contain optional ingredients, such as for example, silane adhesion promoters and fumed silica. Sealants and/or adhesives may be in, various forms, including for example, clear, transparent, translucent or opaque caulks. Typical formulations are found in U.S. Pat. No. 4.626,567 which discloses an acrylic copolymer latex sealant composition, which comprises an acrylic copolymer. Sealants and adhesive may also include, if desired, plasticizers, freeze-thaw stabilizers, colorants or pigments, pigment dispersants, anti-bacterial and/or anti-fungal materials, biocides, mildewcides, preservatives, mineral oils, pH adjusting agents (mineral and organic acids/bases), solvents (e.g. ethylene glycol, propylene glycol), epoxysilanes, and agents for improving rheological properties such as thickeners and anti-slump agents. Plasticizers are generally used in an amount of up to about 25% by weight and the other additives when present, will typically total up to about 3% by weight, based on the total weight of the composition. Plasticizer are often desirable to reduce the tack of the copolymer so that the sealant can have the desired tack-free time of less than 72 hours.

Typical polymer latex sealant compositions have viscosity of 80,000–400,000 cps. The polymer latex can be a totally acrylic polymer latex, a vinyl acetate-ethylene (VAE) copolymer latex or any of the polymer latexes typically used in the art for making sealant compositions, especially caulks.

The plasticizer used may be a diester of phthalic acid or an N-alkyl arylsulfonamide, or mixtures of the two. Suitable diesters of phthalic acid include $C_1$–$C_8$ alkyl arylphthalates such as butyl benzylphthalate, ethyl benzylphthalate, hexyl phenylphthalate, and ethylhexyl phenylphthalate. Suitable N-alkyl arylsulfonamides include N-($C_{1-8}$)alkyl arylsulfonamides such as N-n-butyl benzenesulfonamide. N-n-butyl toluenesulfonamide, N-ethyl benzenesulfonamide, and N-iso-butyl benzylsulfonamide.

Other optional ingredients include silane adhesion promoters, which can be any of those well-known in the art including gamma-mercaptopropyltrimethoxysilane, gamma-glycidoxypropyltrimethoxysilane, gamma-aminopropyltriethoxysilane and mixtures thereof. Suitable silanes also include the organo-amino silanes disclosed in U.S. Pat. No. 4,340,524.

Optional silica may be a hydrophilic fumed silica or it may be a hydrophobic fumed silica derivative in which some of the hydroxyl groups on the surface of the fumed silica have been replaced by trimethylsiloxyl groups. Such hydrophobic silicas are known as silica silylates and are commercially available. Suitable thickeners which may be used include poly(oxy-1,2-ethanediyl)-alpha-hydro-omega-hydroxy polymer with oxy-1,2-ethanediyl-alpha-hydro-omega-hydroxy-nonyl-phenoxyglycidyl ether oligomers and 5-isocyanato-1-(iso-cyanatomethyl)-1,3,3-trimethylcyclohexane or hydroxyethyl cellulose or polyacrylic acid polymers and copolymers or a base such as sodium hydroxide to raise the pH if sufficient carboxylate is present in the system.

The sealants and adhesives may contain residual polymerizable surface active agent, additional polymerizable surface active agent or less preferably, optional traditional anionic, nonionic or amphoteric surfactants, or mixtures thereof, may also be present in the finished sealant or adhesive. Suitable traditional surfactants include those mentioned herein. Filers may be optionally employed in the present invention, such as any conventional inorganic filler, e.g. carbonates, oxides and sulphates. Suitable fillers include calcium carbonate, calcium oxide, magnesium carbonate, barium sulfate and the like. When present, the filler may be about 10 to about 30 wt %, based on total weight of the composition. The sealant composition may also include if desired a freeze-thaw stabilizer, a biocide, fillers and a tooling aide well known in the art. The sealant composition may be readily prepared using a conventional mixer, followed by deairing. Mixing and deairing procedures are well known in the art.

All documents, e.g., patents and journal articles, cited above or below are hereby incorporated by reference in their entirety.

In the following examples, all amounts are stated in percent by weight unless indicated otherwise.

One skilled in the art will recognize that modifications may be made in the present invention without deviating from the spirit or scope of the invention. The invention is illustrated further by the following examples which are not to be construed as limiting the invention or scope of the specific procedures or compositions described herein. All documents, e.g., patents and journal articles, cited above or below are hereby incorporated by reference in their entirety.

As used in the Examples appearing below, the following designations, symbols, terms and abbreviations have the indicated meanings:

| Material | Definition |
| --- | --- |
| Polystep ® A-13 | Linear dodecylbenzene sulfonic acid (commercially available from Stepan Company, Northfield Illinois) |
| Polystep ® A-16 | Branched dodecylbenzene sulfonic acid, sodium salt (commercially available from Stepan Company, Northfield Illinois) |
| Polystep ® A-17 | Branched dodecylbenzene sulfonic acid (commercially available from Stepan Company, Northfield Illinois) |
| Polystep ® B-330A | Ammonium laureth-3-sulfate (commercially available from Stepan Company, Northfield Illinois) |
| Polystep ® AU-7 | Allylammonium laureth-3-sulfate (commercially available from Stepan |

| Material | Definition |
|---|---|
| | Company, Northfield Illinois) |
| Cedephos ® CP-610 | Nonyl Phenol 9-EO Phosphoric Acid Ester (commercially available from Stepan Company, Northfield Illinois) |
| BTC ® 835 | 50% aqueous n-(50% (by weight) $C_{14}$, 40% $C_{12}$ and 10% $C_{16}$)alkyl dimethyl benzyl ammonium chloride |

The amount of agglomerated polymers, or "coagulum", in the resulting lattices at the conclusion of the polymerization is determined by collecting the agglomerated polymers using a 20 mesh screen that has openings sufficiently large enough to allow the discrete un-agglomerated polymers to pass, rinsing the collected agglomerated polymers with water, and weighting the remaining agglomerated polymers trapped on the screen. The percent coagulum is calculated by dividing the weight of the coagulum by the theoretical weight of the entire latex based upon the weights of the ingredients used for the polymerization reaction.

The viscosity of the resulting lattices following polymerization is determined by using a RV Brookfield synchrolechtric viscometer equipped with a No. 3 spindle. During such determinations 950 ml of each latex is placed in a 1000 ml beaker and the viscometer operated at 25° C. and 60 rpm.

Solids of lattices were determined by concentrating the latex at 120° C. in an oven to remove all volitiles, and subsequently weighing the residue. The pH of each solution was measured using an Orion 210 pH meter.

The particle size of the resulting lattices is determined with a NICOMP 370C Auto-dilution particle size analyzer using standard methods and procedures for operation of such equipment and such data recorded for 50% volume in units of nano-meters.

In the following examples, all amounts are stated in percent by weight of active material unless indicated otherwise. One skilled in the art will recognize that modifications may be made in the present invention without deviating from the spirit or scope of the invention. The invention is illustrated further by the following examples which are not to be construed as limiting the invention or scope of the specific procedures or compositions described herein.

EXAMPLE 1

Preparation of n-alkyl dimethyl benzyl ammonium vinyl sulfonate (ADBAVS)

The following example is prepared essentially according to the procedures set forth in U.S. Pat. No. 2,725,326.

To a 1000-mL round-bottomed flask was added BTC® 835 (175 g, 250 mmol, as a 51.3% solution in water) and sodium vinyl sulfonate ((SVS) 130 g, 250 mmol, as a 25% solution in water). The mixture was heated with stirring to 70 C. for 2 hours. Stirring was stopped and the solution seperated to two phases. The bottom water layer was removed and analyzed for Cl⁻ content. The upper organic phase was then subjected to more sodium vinyl sulfonate (65 g, 125 mmol, as a 25% solution in water). The mixture was again heated with stirring to 70 C. for 2 hours. Stirring was stopped and the solution again seperated to two phases. The bottom water layer was removed and analyzed for Cl- content. If the reaction was complete, the upper organic phase was isolated as a viscous liquid and used in the subsequent polymerization step. (The SVS addition step may be repeated as often as needed to achieve desired conversions.) ¹H NMR: δ 7.7 (m, 2H), 7.4 (m, 3H), 6.55 (dd, 1H), 5.81 (dd, 1H), 5.25 (dd, 1H), 4.75 (s, 2H), 3.35 (s, 6H), 1.6–1.9 (m, 3H), 1.3 (m, 22H), 0.9 (t, 3H)

EXAMPLE 2

Preparation of Polymers

1. POLYMER A

Emulsion polymer formed with sodium lauryl sulfate as the only surfactant: Methylmethacrylate-butylacrylate-methacrylic acid (48\48.9\3.1) co-polymer with sodium lauryl sulfate surfactant at 1.5% based on total monomers An initial waterphase consisting of deionised water (328 g) and with sodium lauryl sulfate [(5.65 g), 100%] was placed in a reactor suitable for emulsion polymerization. The reactor was then purged with nitrogen (99% pure), and then heated to between 76–78° C.

Once the internal temperature reached 75–78° C., 20% of the monomers (from the total of 376.6 g) was placed in the reactor. Once the internal temperature equilibrated to 77–79° C.,20% of the ammonium persulphate initiator from the total containing (1.86 g in 79.7 g of deionised water) was started. There is strong exotherm of about 19° C. Once the exotherm was over the additions of the monomers (301.3 g)was started as well as the remaining initiator solution of ammonium persulphate. The temperature of the reaction was kept to between 78–81° C. The additions were continued for two hours. Once the additions were complete, the reactor was cooled to below 30° C., and the emulsion discharged from the reactor and filtered using 420 mesh. The coagulum level was below 0.02%. The polymer was used to cast films for microbiological testing. Solids 50.1%, pH 3.4, Viscosity (4\60) 95 poise.

2. POLYMER B

Methylmethacrylate-butylacrylate-methacrylic acid (48\48.9\3.1) emulsion polymer formed with BTC 835 only at 1.43% and sodium lauryl sulfate at 0.12% based on total monomer content.

An initial waterphase consisting of deionised water (275.8 g) and the BTC 835 [(8.6 g) 50% solution in water] with sodium lauryl sulfate [(0.37 g ) 100% solid] was placed in a reactor suitable for emulsion polymerization. The reactor was then purged with nitrogen (99% pure), and then heated to between 75–77° C.

Once the internal temperature reached 75–78° C., 17.0% of the monomers (from the total of 300 g) was placed in the reactor. Once the internal temperature equilibrated to 75–78° C., 30% of the ammonium persulphate initiator from the total containing (1.62 g in 67.8 g of deionised water) was added over a period of five minutes. A 8–10° C. exotherm was noticeable. Once the exotherm was over the additions of the rest of the monomers (250 g) was started as well as the remaining initiator solution of ammonium persulphate. The temperature of the reaction was kept to between 79–81° C. The additions were continued for one hour.

Samples were taken from the reactor to cast films of the polymer for microbiological testing

3. POLYMER C

Methylmethacrylate-butylacrylate-methacrylic acid (48\48.9\3.1) co-polymer with the ADBAVS at 1.73% and sodium lauryl sulfate at 0.59% based on total weight of monomers.

An initial waterphase consisting of deionised water (270 g) and the ADBAVS [5.41 g, (100%)active], and with sodium lauryl sulfate [(1.1 g), 100%] was placed in a reactor suitable for emulsion polymerization. The reactor was then purged with nitrogen (99% pure), and then heated to between 75–77° C.

Once the internal temperature reached 75–78° C., 20% of the ammonium persulphate initiator from the total containing (1.53 g in 67.8 g of deionised water) was started. Once initiator was added, five minutes later addition of the monomers (143.5 g of butyl acrylate, 158.3 g of methylmethacrylate and 9.3 g of methacrylic acid) was started as well as the rest of the sodium lauryl sulfate (0.67 g in 62.4 g of deionised water) and the remaining initiator solution of ammonium persulphate. The temperature of the reaction was kept to between 78–81° C. The addition was continued for one hour. Once the addition was complete the reactor was cooled to below 30° C., and the emulsion discharged from the reactor and filtered using 420 mesh. The coagulum level was below 0.02%. The polymer was used to cast films for microbiological testing.

EXAMPLE 3

Antimicrobial Activity

Test Organisms
A. Gram Positive Bacteria: *Staphylococcus aureus* (ATCC 6538)
B. Fungi—Yeast: *Candida albicans* (ATCC 10231)
C. Fungi—Mold: *Aspergillus niger* (ATCC 16404)

Media
D/E Neutralizing Broth
Microbial Content Agar
Nutrient Broth—Difco
Phosphate Buffered Water
Sabouraud Dextrose Agar
Sterile Deionized Water Procedures Residual Time Kill—*S. aureus*
1. Centrifuge 24-hour culture of *S. aureus* and re-suspend in sterile phosphate buffered water. Repeat centrifugation and re-suspension of culture twice.
2. Determine total count in 1 ml of inoculum and in uninoculated latex coating samples by standard pour plate procedure using D/E Broth and Microbial Content Agar.
3. Pipet 1 ml of inoculum onto surface of each dried latex coating sample. Spread inoculum over surface of coating using a flamed and cooled inoculating needle. Record time of inoculation. Allow samples to remain at room temperature.
4. Two hours after inoculation, add 10 ml of sterile phosphate buffer to each bottle and shake vigorously. Remove 1 ml of phosphate buffer and determine total count via standard pour plate procedure again using D/E Broth and Microbial Content Agar.
5. Remove remaining 9 ml of phosphate buffer from each bottle, filter through a 0.45 micron filter, and submit for quaternary actives analysis.
6. Rinse each bottle with an additional 10 ml of sterile phosphate buffer and discard buffer.
7. Repeat steps 2–6 twice.
8. Twenty-four hours after the initial inoculation, repeat steps 1–7 using the same latex coating samples previously tested.
9. Incubate plates for 48–54 hours at 35+1° C.
10. Determine percent reduction after 2 hours as follows:
Calculation of Percent Kill:

$$\frac{X-Y}{X} \times 100\% = \% \text{ kill}$$

where:
X=Initial inoculum control count
Y=Test substance bacterial count after 2 hours contact Residual Time Kill—*A. niger* and *C. albicans*
1. Centrifuge 24 hour broth culture of *C. albicans* and 10 day *A. niger* spore suspension. Re-suspend culture in sterile phosphate buffered water. Repeat centrifugation and re-suspension of culture twice.
2. Determine total count in 1 ml of inoculum and in uninoculated latex coating samples by standard pour plate procedure using D/E Broth and Sabouraud Dextrose Agar.
3. Pipet 1 ml of inoculum onto surface of each dried latex coating sample. Spread inoculum over surface of coating using a flamed and cooled inoculating needle. Record time of inoculation.
4. Six hours after inoculation, add 10 ml of sterile phosphate buffer to each bottle and shake vigorously. Remove 1 ml of phosphate buffer and determine total count via standard pour plate procedure again using D/E Broth and Sabouraud Dextrose Agar.
5. Remove remaining 9 ml of phosphate buffer from each bottle, filter through a 0.45 micron filter, and submit for quaternary actives analysis.
6. Rinse each bottle with an additional 10 ml of sterile phosphate buffer and discard buffer.
7. Twenty-four hours after the initial inoculation, repeat steps 1–6 using the same latex coating samples previously tested.
8. Incubates plates at 28±1° C. for 5–7 days.
9. Determine percent reduction after 6 hours as follows:
Calculation of Percent Kill:

$$\frac{X-Y}{X} \times 100\% = \% \text{ kill}$$

where:
X=Initial inoculum control count
Y=Test substance fungal count after 6 hours contact The results provided in Table I show that POLYMER C demonstrated sustained high level (i.e. >96%) bactericidal and fungicidal activity throughout the test period. Structural integrity of the test films was maintained throughout the study.

POLYMER B demonstrated significant efficacy against *S. aureus* during the first three challenge cycles. During challenge cycles 4–6 biocidal activity diminished considerably. Coating integrity for this group of samples was generally poor. Noticeable coating losses were noted throughout the study, but most noticabily during rinses 4–6.

POLYMER C demonstrated strong levels of activity against *C. albicans* at both 6-hour sampling periods. These samples were however only minimally effective against *A. niger*.

POLYMER A demonstrated poor biocidal and residual biocidal activity against all test organisms.

TABLE II

RESIDUAL TIME-KILL TESTING OF ANTIMICROBIAL LATEX COATINGS

| Sample Identifier | Test Organism | Challenge Number[1] | | | | | | | | | | | |
|---|---|---|---|---|---|---|---|---|---|---|---|---|---|
| | | 1 | | 2 | | 3 | | 4 | | 5 | | 6 | |
| | | TVC | % Kill | TVC | % Kill | TVC | % Kill | TVC | % Kill | TVC | % Kill | TVC | % Kill |
| POLYMER B | S. aureus | <1000 | >99.9 | <1000 | >99.9 | 390000 | 90.9 | 2900000 | 25.6 | 3200000 | 15.8 | 3500000 | 14.6 |
| | A. niger | 12000000 | 0.0 | 8000000 | 80.0 | | | | | | | | |
| | C. albicans | <1000 | >99.9 | 120000 | 99.1 | | | | | | | | |
| POLYMER C | S. aureus | <1000 | >99.9 | <1000 | >99.9 | <1000 | >99.9 | <1000 | >99.9 | <1000 | >99.9 | <1000 | >99.9 |
| | A. niger | 300000 | 96.3 | 100000 | 99.8 | <1000 | | | | | | | |
| | C. albicans | | >99.9 | <1000 | >99.9 | | | | | | | | |
| POLYMER A | S. aureus | $3.9 \times 10^6$ | 9.3 | $3.7 \times 10^6$ | 22.9 | $3.0 \times 10^6$ | 30.2 | $3.3 \times 10^6$ | 15.4 | $3.4 \times 10^6$ | 10.5 | $3.5 \times 10^6$ | 14.6 |
| | A. niger | $1.4 \times 10^6$ | 0.0 | $1.0 \times 10^6$ | 75.0 | | | | | | | | |
| | C. albicans | $1.4 \times 10^6$ | 12.5 | $1.3 \times 10^6$ | 0.0 | | | | | | | | |
| POLYMER B | Uninoculated | Bacterial and Fungal Count: <10 cfu/sample | | | | | | | | | | | |
| POLYMER C | Controls | Bacterial and Fungal Count: <10 cfu/sample | | | | | | | | | | | |
| POLYMER A | | Bacterial and Fungal Count: <10 cfu/sample | | | | | | | | | | | |

*Test Temperature: 25–27° C.
[1]Challenge Number = number of inoculation/rinse sequence
S. aureus each challenge represents a 2 hour contact period
A. niger and C. albicans each challenge represents a 6 hour contact period
TVC = Total Viable Count, cfu/bottle From the foregoing, it will be appreciated that although specific embodiments of the invention have been described herein for purposes of illustration, various modifications may be made without deviating from the spirit or scope of the invention.

What is claimed is:

1. An antimicrobial material comprising a latex comprising polymer particles and a primary surfactant component, where the primary surfactant is an anionic surfactant, and the polymer particles comprise
    (a) at least one monomer unit; and
    (b) at least one surface active agent unit, wherein
    the monomer unit is derived from an ethylenically unsaturated monomer;
    the surface active agent unit is derived from a polymerizable antibacterial quaternary ammonium compound; and
    the ethylenically unsaturated monomer and the polymerizable antibacterial quaternary ammonium compound have reacted to form polymer particles.

2. A material according to claim 1, wherein the polymerizable antibacterial quaternary ammonium compound comprises an antibacterial quaternary ammonium portion and an anion of an ethylenically unsaturated acid.

3. A material according to claim 2, wherein the ethylenically unsaturated acid is a sulfonic, carboxylic, or phosphoric acid covalently bound to an organic moiety having at least one site of unsaturation.

4. A material according to claim 3, wherein the ethylenically unsaturated acid is selected from the group consisting of:
    unsaturated sulfonic acids, unsaturated polysulfonic acids, unsaturated sulfonic acids of oils, unsaturated paraffin sulfonic acids, unsaturated lignin sulfonic acids, unsaturated petroleum sulfonic acids, unsaturated tall oil acids, unsaturated olefin sulfonic acids, unsaturated hydroxyolefin sulfonic acids, unsaturated polyolefin sulfonic acids, unsaturated polyhydroxy polyolefin sulfonic acids, unsaturated carboxylic acids, unsaturated perfluorinated carboxylic acids, unsaturated carboxylic acid sulfonates, unsaturated alkoxylated carboxylic acid sulfonic acids, unsaturated polycarboxylic acids, unsaturated polycarboxylic acid polysulfonic acids, unsaturated alkoxylated polycarboxylic acid polysulfonic acids, unsaturated phosphoric acids, unsaturated alkoxylated phosphoric acids, unsaturated polyphosphoric acids, and unsaturated alkoxylated polyphosphoric acids, unsaturated fluorinated phosphoric acids, unsaturated phosphoric acid esters of oils, unsaturated phosphinic acids, unsaturated alkylphosphinic acids, unsaturated aminophosphinic acids, unsaturated polyphosphinic acids, unsaturated vinyl phosphinic acids, unsaturated phosphoric acids, unsaturated polyphosphonic acids, unsaturated phosphoric acid alkyl esters, unsaturated α-phosphono fatty acids, unsaturated oragnoamine polymethylphosphonic acids, unsaturated organoamino dialkylene phosphoric acids, unsaturated alkanolamine phosphoric acids, unsaturated trialkyledine phosphonic acids, unsaturated acylamidomethane phosphoric acids, unsaturated alkyliminodimethylene diphosphonic acids, unsaturated polymethylene-bis (nitrilodimethylene) tetraphosphonic acids, unsaturated alkyl bis (phosphonoalkylidene) amine oxide acids, unsaturated esters of substituted aminomethylphosphonic acids, unsaturated phosphonamidic acids, unsaturated acylated amino acids, unsaturated N-alkyl acylamino acids, and unsaturated acylated protein hydrolysates, and mixtures thereof.

5. A material according to claim 3, wherein the ethylenically unsaturated acid is selected from the group consisting of:
    vinyl sulfonic acids, vinyl sulfinic acids, vinyl sulfenic acids, vinyl sulfonic acid esters, vinyl carboxylic acids, vinyl phosphoric acids, vinyl phosphonic acids, vinyl phosphinic, vinyl phosphenic acids, and mixtures thereof.

6. A material according to claim 3, wherein the ethylenically unsaturated acid is vinyl sulfonic acid.

7. A material according to claim 1, wherein the primary surfactant component is an alkoxylated alkyl sulfuric acid ester.

8. A material according to claim 2 wherein the antibacterial quaternary ammonium portion is n+($C_8$–$C_{20}$) alkyl di ($C_1$–$C_7$) benzyl ammonium.

9. A material according to claim 2 wherein the antibacterial quaternary ammonium portion is n+(50% (by weight) $C_{14}$, 40% $C_{12}$ and 10% $C_{16}$) alkyl dimethyl benzyl ammonium.

10. A material according to claim 2 wherein the antibacterial quaternary ammonium portion is 34% by weight $C_{12}$ and 16% by weight $C_{14}$ n-alkyl dimethyl ethylbenzyl ammonium and about 30% by weight $C_{14}$, 15% by weight $C_{16}$, 2.5% by weight $C_{12}$ and 2.5% by weight $C_{18}$ n-alkyl dimethyl benzyl ammonium.

11. A material according to claim 1, wherein the ethylenically unsaturated monomer is selected from methylmethacrylate, butylacrylate and methacrylic acid.

12. A material according to claim 1, wherein the ethylenically unsaturated monomer is a mixture of methylmethacrylate, butylacrylate and methacrylic acid.

13. A material according to claim 3, wherein the ethylenically unsaturated acid is a vinyl sulfonic acid, vinyl carboxylic acid, or vinyl phosphoric acid.

14. A material according to claim 1, which is a paint further comprising pigment.

15. A material according to claim 1, which is a caulk further comprising pigment, plasticizer, and thickener. vinyl sulfonic acid, vinyl carboxylic acid, or vinyl phosphoric acid.

16. A material according to claim 15, further comprising an adhesion promoter.

17. A material according to claim 1, wherein at least one of the monomers is styrene and is reacted with at least one acrylic monomer.

18. A material according to claim 1, wherein at least one of the monomers is at least one non-aromatic vinyl compound.

19. A material according to claim 1, wherein at least one of the monomers is vinyl acetate and is reacted with at least one acrylic monomer.

20. A material according to claim 1, wherein at least one of the monomers is at least one acrylic monomer.

21. A material according to claim 1, wherein the polymerizable antibacterial quaternary ammonium compound and the monomer are in a ratio of about 0.01:1 to about 3.1 on a weight basis, prior to polymerization.

22. A material according to claim 1, wherein the polymerizable antibacterial quaternary ammonium compound comprises about 0.1–10 weight percent of the polymer, based on the total weight of the monomer present prior to polymerization.

23. A material according to claim 22, wherein the polymerizable antibacterial quaternary ammonium compound comprises about 0.5–3.0 weight percent of the polymer, based on the total weight of the monomer present prior to polymerization.

* * * * *